United States Patent
Athanasiou et al.

(10) Patent No.: US 11,865,395 B2
(45) Date of Patent: Jan. 9, 2024

(54) MOVEMENT THERAPY APPARATUS

(71) Applicant: Neurofenix Limited, Stratford-Upon-Avon (GB)

(72) Inventors: Dimitris Athanasiou, London (GB); Guillem Singla Buxarrais, London (GB); Federico Casarini, London (GB); Etienne Burdet, London (GB)

(73) Assignee: Neurofenix Limited, Stratford-Upon-Avon (GB)

( * ) Notice: Subject to any disclaimer, the term of this patent is extended or adjusted under 35 U.S.C. 154(b) by 79 days.

(21) Appl. No.: 16/956,508

(22) PCT Filed: Dec. 19, 2018

(86) PCT No.: PCT/GB2018/053703
§ 371 (c)(1),
(2) Date: Jun. 19, 2020

(87) PCT Pub. No.: WO2019/122885
PCT Pub. Date: Jun. 27, 2019

(65) Prior Publication Data
US 2021/0008410 A1    Jan. 14, 2021

(30) Foreign Application Priority Data

Dec. 19, 2017  (GR) .............................. 20170100582
Jan. 19, 2018  (GB) ..................................... 1800910
(Continued)

(51) Int. Cl.
*A63B 23/16*    (2006.01)
*A63B 21/00*    (2006.01)
(Continued)

(52) U.S. Cl.
CPC ............ *A63B 23/16* (2013.01); *A63B 21/028* (2013.01); *A63B 21/4019* (2015.10);
(Continued)

(58) Field of Classification Search
CPC .......... A63B 21/0004; A63B 21/00058; A63B 21/00061; A63B 21/00065;
(Continued)

(56) References Cited

U.S. PATENT DOCUMENTS 5,433,407 A * 7/1995 Rice ................... A47B 21/0371
248/118.1
6,093,159 A * 7/2000 Racoosin ........... A61H 15/0092
601/118

(Continued)

FOREIGN PATENT DOCUMENTS

DE      202011110221    5/2013
WO      WO2015057162    4/2015
WO      WO-2015057162 A1 *  4/2015    ............. A63B 23/16

OTHER PUBLICATIONS

PCT International Preliminary Report on Patentability in PCT/GB2018/053703, titled "Movement Training Apparatus", Applicant Neurofenix Limited, filed Dec. 19, 2018.
(Continued)

*Primary Examiner* — Sundhara M Ganesan
*Assistant Examiner* — Zachary T Moore
(74) *Attorney, Agent, or Firm* — Mahamedi IP Law LLP

(57) ABSTRACT

An apparatus for movement therapy, and more specifically, an apparatus for movement and function therapy of the hand and arm and particularly for use in rehabilitation of the hand following a stroke or other neurological or physical impairments. The invention extends to a corresponding system, method, and kit of parts.

19 Claims, 34 Drawing Sheets

(30) Foreign Application Priority Data

May 10, 2018 (GB) ..................................... 1807643
Oct. 10, 2018 (GB) ..................................... 1816507

(51) Int. Cl.
*A63B 21/02* (2006.01)
*A63B 24/00* (2006.01)

(52) U.S. Cl.
CPC ...... *A63B 21/4035* (2015.10); *A63B 24/0062* (2013.01); *A63B 2220/20* (2013.01); *A63B 2220/40* (2013.01); *A63B 2220/51* (2013.01); *A63B 2220/802* (2013.01); *A63B 2220/805* (2013.01); *A63B 2220/833* (2013.01)

(58) Field of Classification Search
CPC ........ A63B 21/00069; A63B 21/00178; A63B 21/00189; A63B 21/002; A63B 21/0023; A63B 21/026; A63B 21/045; A63B 21/0455; A63B 21/055; A63B 21/159; A63B 21/4011; A63B 21/4017; A63B 21/4019; A63B 21/4021; A63B 21/4033; A63B 21/4035; A63B 21/4043; A63B 21/4045; A63B 23/035; A63B 23/03508; A63B 23/12; A63B 23/14; A63B 23/16; A63B 24/0062; A63B 24/0075; A63B 2024/0068; A63B 2024/0071; A63B 2024/0081; G06F 3/033; G06F 3/0354; G06F 3/03541; G06F 3/03543; G06F 3/03544; G09B 13/00
See application file for complete search history.

(56) References Cited

U.S. PATENT DOCUMENTS

| | | | |
|---|---|---|---|
| 7,063,646 B1* | 6/2006 | Slimi | A63B 22/14 |
| | | | 482/141 |
| 10,592,008 B1* | 3/2020 | Wang | G06F 3/0346 |
| 10,748,437 B2* | 8/2020 | Lynch | G09B 23/28 |
| 11,260,264 B2* | 3/2022 | Richter | A63B 21/4021 |
| 2006/0014615 A1* | 1/2006 | Godbold | A63B 21/4035 |
| | | | 482/141 |
| 2006/0164392 A1* | 7/2006 | Mao | G06F 3/03543 |
| | | | 345/163 |
| 2017/0296864 A1* | 10/2017 | Richter | A63B 21/072 |
| 2018/0074603 A1* | 3/2018 | Popescu | G06F 3/041 |
| 2019/0167504 A1* | 6/2019 | Polygerinos | A63B 21/0023 |

OTHER PUBLICATIONS

PCT International Search Report and Written Opinion in PCT/GB2018/053703, titled "Movement Training Apparatus", Applicant Neurofenix Limited, filed Dec. 19, 2018.
European Patent Office Examination Report dated Oct. 11, 2021, in application No. 18 829 452.4-1222.

* cited by examiner

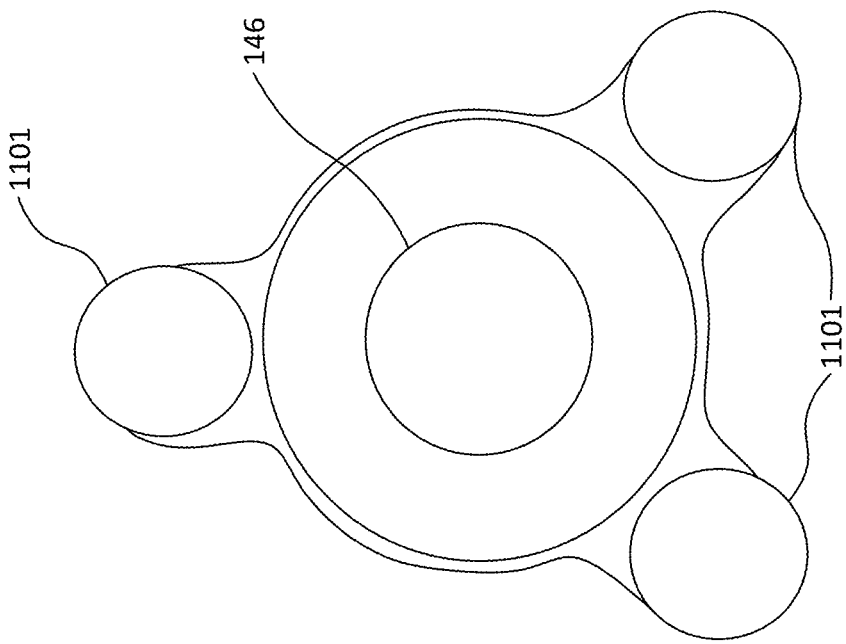
Figure 11k
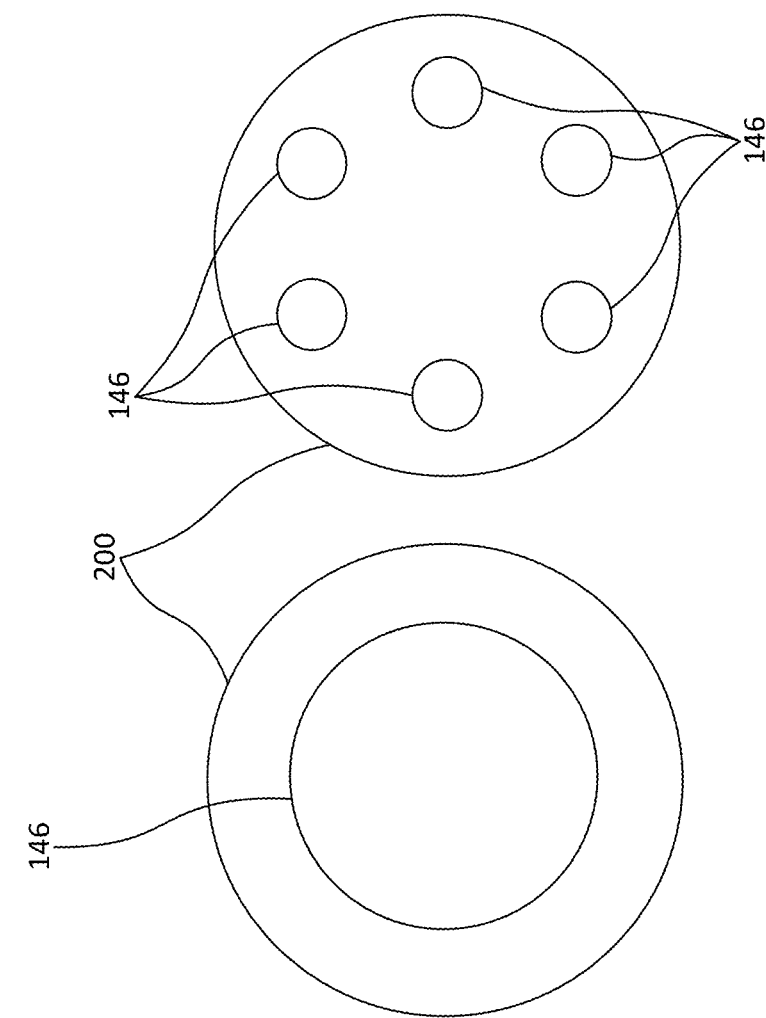
Figure 11j
Figure 11i

MOVEMENT THERAPY APPARATUS

FIELD OF THE INVENTION

The present invention relates to an apparatus for movement therapy, and more specifically, an apparatus for movement and function therapy of the hand and arm. In particular, the invention relates to an apparatus for use in rehabilitation of the hand following a stroke or other neurological or physical impairments. The invention extends to a corresponding system, method, and kit of parts.

BACKGROUND

Stroke survivors often experience at least some loss of motor function, generally along one side of the body, which can cause difficulty when performing everyday tasks. Physiotherapy is a proven method of rehabilitation that can assist stroke survivors in recovering motor function; however, access to physiotherapy is limited by available physiotherapists.

Several different apparatuses have been proposed to help retrain finger, wrist, forearm, and shoulder—the 'upper limb' movement of stroke survivors and/or those with a neurological or physical impairment, and the present invention seeks to improve on these by providing an accessible apparatus which can be used independently or with minimum assistance from carers or stroke care professionals, such as therapists.

SUMMARY

Aspects and embodiments of the present invention are set out in the appended claims. These and other aspects and embodiments of the invention are also described herein.

According to one aspect of the invention, there is provided an apparatus for training hand movement, comprising: a base arranged to support a hand; and at least one finger support provided on the base; wherein the at least one finger support is independently movable relative to the base.

According to one aspect of the invention, there is provided an apparatus for training hand movement, comprising: a base arranged to support a hand; and at least one finger support provided on the base; a finger and/or hand restraint; and wherein the at least one finger support is independently movable relative to the base.

It is understood that the finger and/or hand restraint may be used to refer to any other limb or body part restraint, for example a foot restraint.

Optionally, the at least one finger support is arranged to allow the hand to exert a grasping motion on the base.

Optionally, the at least one finger support is arranged to allow an extension movement to be exerted thereon by the finger of a user.

Optionally, the at least one finger support has a neutral position relative to the base, said at least one support being arranged to resist movement away from the neutral position.

Optionally, the at least one finger support is formed from a resilient material thereby to resist movement away from the neutral position.

Optionally, the at least one finger support is arranged to be biased into the neutral position, preferably wherein the position of the neutral position relative to the base is adjustable.

Optionally, the at least one finger support is deployable from a stored position into the neutral position.

Optionally, the at least one finger support is removably attachable to the base.

Optionally, the apparatus comprises two or more finger supports, preferably wherein said finger supports are configured to move and/or be removably attached to the base independent of one another.

Optionally, the base comprises a plurality of mounts for the finger supports, preferably wherein the mounts are configurable to attach the at least one finger support to the base such that the apparatus can selectively be used by both a left-handed and a right-handed user.

Optionally, the at least one finger support is an elongate member arranged to extend away from the base when attached thereto.

Optionally, the at least one finger support is capable of being deflected by a finger, for example by deformation of the elongate member.

Optionally, the at least one finger support comprises a material having a non-constant stiffness, for example a stiffness that varies along the length of the elongate member.

Optionally, the at least one finger support comprises an arrangement for retaining a finger to said support. Optionally, the at least one finger support comprises an optionally detachable arrangement for retaining a finger to said support.

Optionally, the apparatus further comprises a mounting arranged to receive the base, whereby the base is movable relative to the mounting.

Optionally, the base and mounting are arranged such that movement of the base relative to the mounting can be restricted to at least one of x, y and z axes of rotation.

Optionally, there is provided a modular block and one or more recesses on the base and/or mounting to at least partially accommodate the modular block.

Optionally, the modular block is operable to restrict movement of the base relative to movement of the mounting.

Optionally, the modular block is operable to be coupled to the base.

Optionally, there is provided at least one support arranged to provide a cushioning effect on the hand. Optionally, the support is formed from one or more of: silicone; thermoplastic polyurethane (TPU); thermoplastic elastomer (TPE); and/or foam.

Optionally, the base comprises one or more apertures, optionally wherein the one or more apertures are used for ventilation.

A further aspect of the present invention provides an apparatus for training hand movement, comprising: a base arranged to support a hand; a mounting arranged to receive the base such that the base is movable relative to the mounting; wherein the base and mounting are arranged such that movement of the base relative to the mounting can be restricted to at least one of x, y and z axes of rotation.

Optionally, the base is pivotable relative to the mounting about a single axis of rotation.

Optionally, the base is arranged to pivot relative to the mounting about two of said axes of rotation.

Optionally, the base is arranged to pivot relative to the mounting about all three of said axes of rotation.

Optionally, the axes of rotation are orthogonal.

Optionally, the mounting may be positioned such that the axes of rotation about which the base can move are respectively aligned with a direction of a motion of the hand of a user, for example when in use.

Optionally, the motion of the base relative to the mounting is arranged to simulate at least one of the following movements: wrist flexion/extension; forearm pronation/supination; and wrist ulnar and radial deviation.

Optionally, configuration of the axes about which the base can move relative to the mounting is manually selectable.

Optionally, the configuration of the axes about which the base can move relative to the mounting is configured automatically in response to an input signal received from a computing device.

Optionally, the mounting is arranged to have a recess into which the base is received such that the base can rotate relative to the mounting.

Optionally, the mounting is further arranged such that a limb may be supported above the recess.

Optionally, the base is provided with at least one groove arranged to extend in a linear direction across at least a portion of the base, and wherein the mounting comprises a formation arranged to engage with the at least one groove so as to restrict the movement of the base relative to the mounting.

Optionally, the mounting comprises an outer portion and an inner portion arranged to receive the base, the inner and outer portions being configured such that the inner portion can move relative to the outer portion.

Optionally, the mounting is arranged to inhibit movement of the base, preferably wherein the mounting is operable to retain the base in a fixed position.

Optionally, the apparatus further comprises a means for assisting or resisting movement of the base relative to the mounting.

Optionally, the base is removably mountable to the mounting.

Optionally, the base has a generally spherical configuration, and preferably wherein the mounting comprises a semi-spherical recess for receiving the base.

Optionally, the base comprises a top substantially hemispherical part and a bottom substantially hemispherical part.

Optionally, the bottom substantially hemispherical part comprises one or more electronic components.

Optionally, the top substantially hemispherical part is disposable.

Optionally, the bottom substantially hemispherical part is operable to be fitted to one or more of a user's: chest; waist, leg; arm; head; and/or neck.

Optionally, the bottom substantially hemispherical part is operable to be coupled with another part or device to allow the training of other joints or parts of the human body.

Optionally, the base is of a substantially cylindrical shape.

Optionally, the base comprises a flattened and/or cut-out section for supporting the hand when at least one finger of the user is received by the at least one finger support.

Optionally, the base is arranged to support at least one of the heel and palm of a hand.

Optionally, the apparatus further comprises at least one sensor for acquiring data related to movement of (the) at least one finger support relative to the base.

Optionally, the apparatus further comprises at least one sensor for acquiring data related to movement of the base relative to the mounting.

Optionally, the at least one sensor is a force and/or displacement sensor.

Optionally, the at least one sensor comprises an inertial measurement unit provided in the base, optionally wherein the inertial measurement unit comprises a gyroscope and/or magnetometer.

Optionally, the base further comprises a vibrating element for providing haptic feedback.

Optionally, the base comprises an internal battery for supplying power to the at least one sensor, wherein the mounting is arranged to charge said battery when the base is mounted to the mounting.

Alternatively, the apparatus comprises an internal battery for supplying power to the at least one sensor, wherein the apparatus is configured to charge said battery.

One aspect of the present invention provides a method for training hand movement, comprising: providing a base arranged to support a hand; and providing at least one finger support arranged to be moved relative to the base between a first position and a second position; wherein the finger support is biased towards the first position.

Optionally, the method provides two or more finger supports arranged to move relative to the base independent of one another.

Optionally, the method provides a mounting arranged to receive the base such that the base is movable relative to the mounting.

One aspect of the present invention provides a method for training hand movement, comprising: providing a base arranged to support a hand; providing a mounting arranged to receive the base such that the base is movable relative to the mounting; and restricting movement of the base to at least one of x, y and z axes of rotation.

Optionally, the base is arranged to pivot relative to the mounting about a single axis of rotation.

Optionally, the base is arranged to pivot relative to the mounting about two (of said) axes of rotation.

Optionally, the base is arranged to pivot relative to the mounting about (all of said) three axes of rotation.

Optionally, the axes of rotation are orthogonal.

Optionally, the axes of rotation are positioned such that axes of rotation about which the base can move is respectively aligned with a direction of a motion of the hand of a user when in use.

One aspect of the present invention provides a system for training hand movement, comprising: a computing device; and an apparatus according to an aspect of the present invention; wherein the computing device is configured to receive an input signal from the apparatus and to use said input signal as a control input for controlling the computing device, said input signal comprising measurement data received from the at least one sensor of the apparatus.

Optionally, the computing device is programmed with a rehabilitation game.

Optionally, the rehabilitation game is a multiplayer game and the computing device is arranged to communicate with another computing device associated with another such apparatus.

One aspect of the present invention provides a kit of parts for training hand movement, comprising: a first base for supporting a hand; a second base for supporting a hand; and a mounting arranged to receive the first or second base, said first and second bases being interchangeable with the mounting; wherein the first base is arranged to be moveable relative to the mounting about a different number of axes of rotation than the second base.

One aspect of the present invention provides a kit of parts for training hand movement, comprising a base for supporting a hand, a first mounting arranged to receive the base for supporting a hand, and a second mounting arranged to receive the base for supporting a hand, the said first and second mountings being interchangeable with the base; wherein the first mounting is arranged allow movement of the base relative to the mounting about a different number of axes of rotation than the second mounting.

The invention extends to methods, system and apparatus substantially as herein described and/or as illustrated with reference to the accompanying Figures.

The invention also provides a computer program or a computer program product for carrying out any of the methods described herein, and/or for embodying any of the apparatus features described herein, and a computer readable medium having stored thereon a program for carrying out any of the methods described herein and/or for embodying any of the apparatus features described herein.

The invention also provides a signal embodying a computer program or a computer program product for carrying out any of the methods described herein, and/or for embodying any of the apparatus features described herein, a method of transmitting such a signal, and a computer product having an operating system which supports a computer program for carrying out the methods described herein and/or for embodying any of the apparatus features described herein.

Any feature in one aspect of the invention may be applied to other aspects of the invention, in any appropriate combination. In particular, method aspects may be applied to apparatus aspects, and vice versa. As used herein, means plus function features may be expressed alternatively in terms of their corresponding structure, such as a suitably programmed processor and associated memory. Furthermore, features implemented in hardware may generally be implemented in software, and vice versa. Any reference to software and hardware features herein should be construed accordingly.

It should also be appreciated that particular combinations of the various features described and defined in any aspects of the invention can be implemented and/or supplied and/or used independently.

BRIEF DESCRIPTION OF THE DRAWINGS

The invention will now be described, purely by way of example, with reference to the accompanying drawings, in which:

FIGS. 1A to 1F illustrate alternative systems for locking or fixing a base on a mounting;

FIGS. 11A to 11K show alternative mountings for the apparatus;

DETAILED DESCRIPTION

Figure 1:
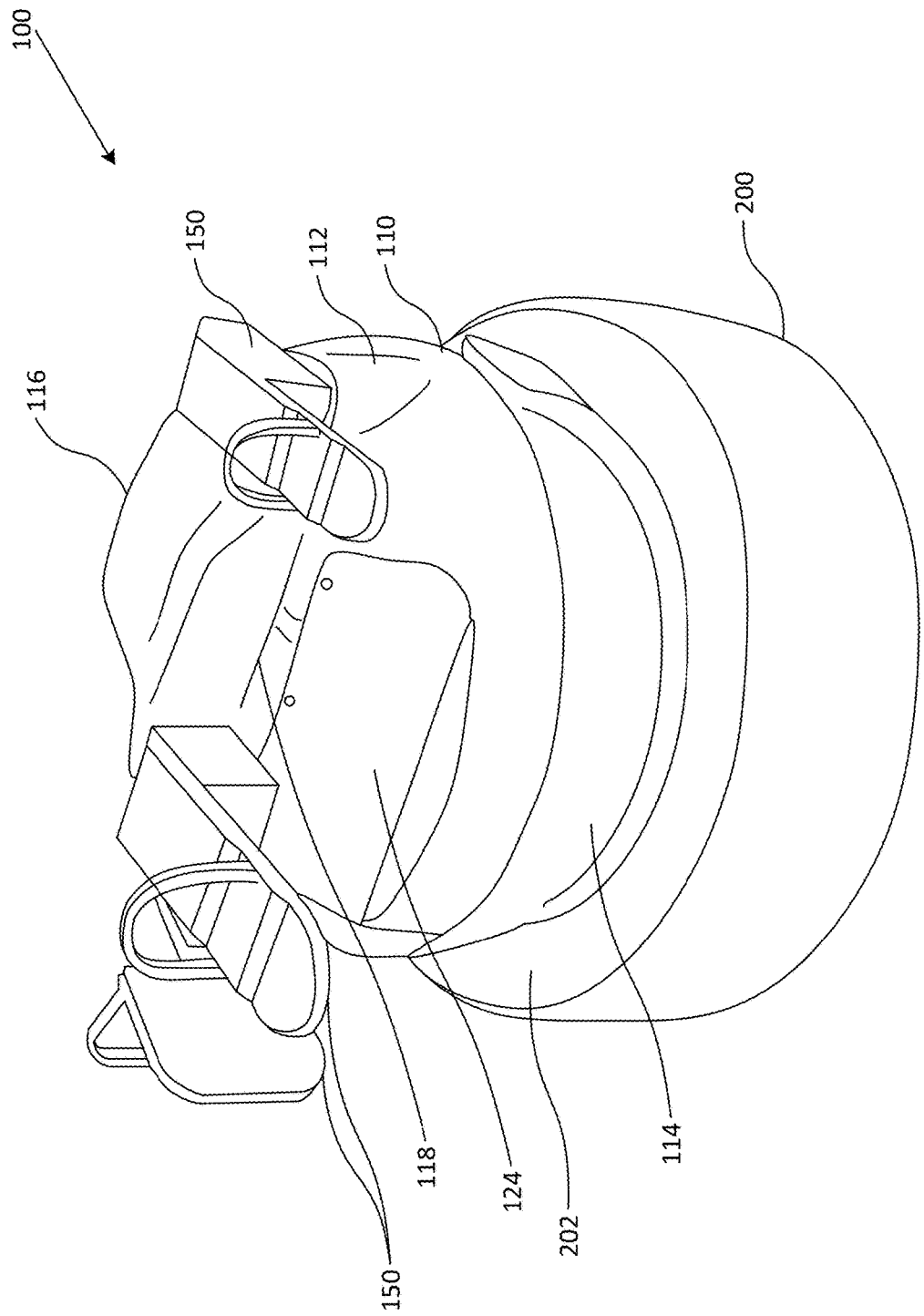
FIG. 1 shows an apparatus according to an aspect of the present invention.

FIG. 1 shows an apparatus 100 according to one aspect of the present invention. The apparatus 100 comprises a generally spherical body 110 (also referred to as a "base" 110), having one or more removable finger supports 150 mounted thereon. The body 110 is formed from an upper hemisphere 112 and a lower hemisphere 114, and may have a diameter of approximately 130 mm (which may allow for portable use).

The apparatus 100 further comprises a mounting 200 upon which the body 110 may be removably supported. The mounting 200 is arranged such that it can be placed stably on a flat surface. A user may thereby use the apparatus 100 with the body 110 in a mounted mode, that is to say it is supported by the mounting, or an unmounted mode, that is to say it is unsupported by the mounting, and detached therefrom. This may allow for additional flexibility in training. The mounting 200 is generally shaped as a shortened cylinder (e.g. "puck-shaped"), with a recess 202 provided on an upper surface of the mounting 200 for receiving a portion of the body 110. The body 110 is movable relative to the mounting 200 when received into the mounting 200. In particular, the body 110 is arranged to rotate within the recess 202 so as to pivot in relation to the mounting 200, as will be described in more detail later on.

The base 110 may be stabilised on the mounting, so that for example a user may thereby place their hand on the base more easily. This may especially assist users who have difficulties putting their hand on the device.

FIGS. 1A to 1E illustrate five different alternative systems for locking or fixing the base 110 on the mounting 200.

Figure 1A:
Figure 1A:
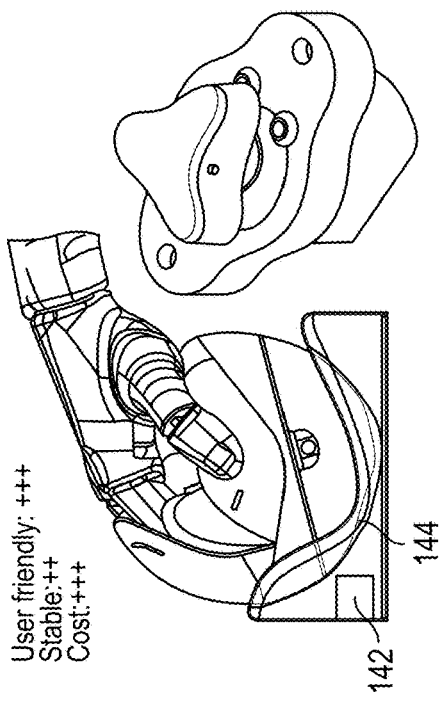

FIG. 1A shows an arrangement in which two hooks 140 are provided on either side of the mounting 200, wherein one hook is coupled to the front of the base 110 and one hook 140 to the back of the base. The front hook is operable to connect to the top cover of the base 110, located above a middle finger of a user, while the back hook is placed to clip onto a lower hemisphere of the base. These hooks 140 may be provided as an integral part of the mounting, or they may be modular and hence attachable or detachable as required. Optionally, this configuration may have more or fewer than two hooks to achieve a similar functionality.

Figure 1B:
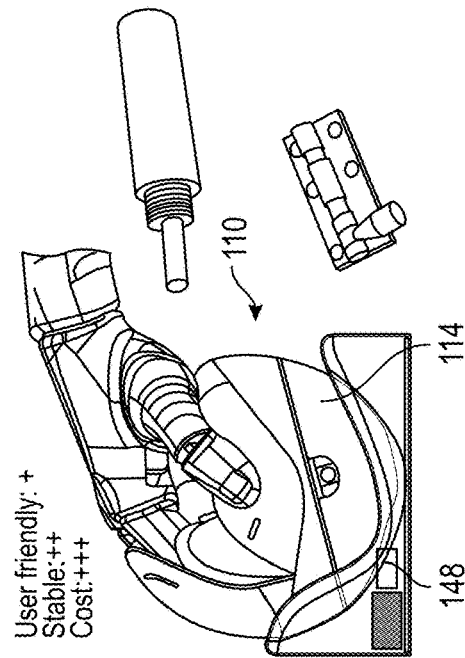

FIG. 1B shows an arrangement whereby the mounting 200 is provided with a magnet 142 whilst the base 110 is provided with a metallic strip 144. Alternatively, or additionally, the mounting 200 may be provided with the metallic strip 144, and the base may be provided with a magnet 142, so as to fix and/or lock the base to the mounting. The magnet 142 may be in the form of a permanent magnet installed as an integrated part of the base 110, as a removable part of the mounting 200 which may be used to disengage the system, or in the form of an electromagnet which can be turned on or off as required.

Figure 1C:
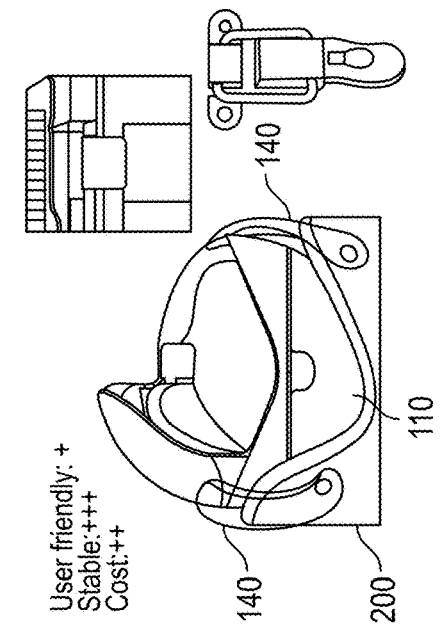

FIG. 1C shows an arrangement whereby a friction pad 146 is provided between the mounting 200 and the base 110. This is a simple way to variably obstruct the movement of the base 110 in the mounting 200.

Figure 1D:
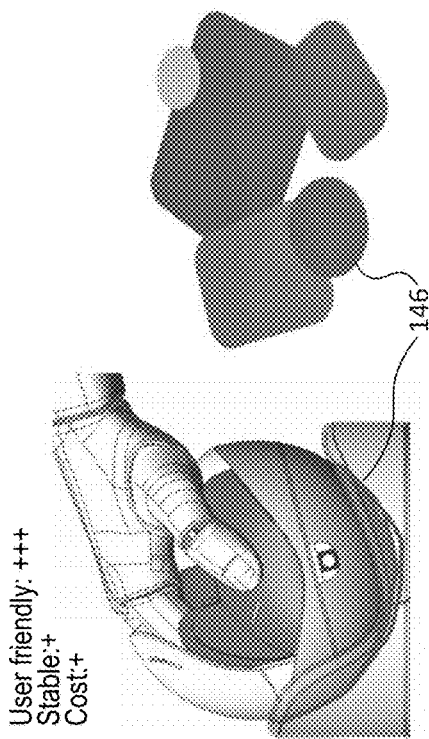

FIG. 1D shows an arrangement wherein a linear pin 148 is provided to lock the base to the mounting. The linear pin 148 may be inserted manually or automatically. When the linear pin 148 is inserted through both the base and the mounting, it can serve to block their relative movement.

Figure 1F:
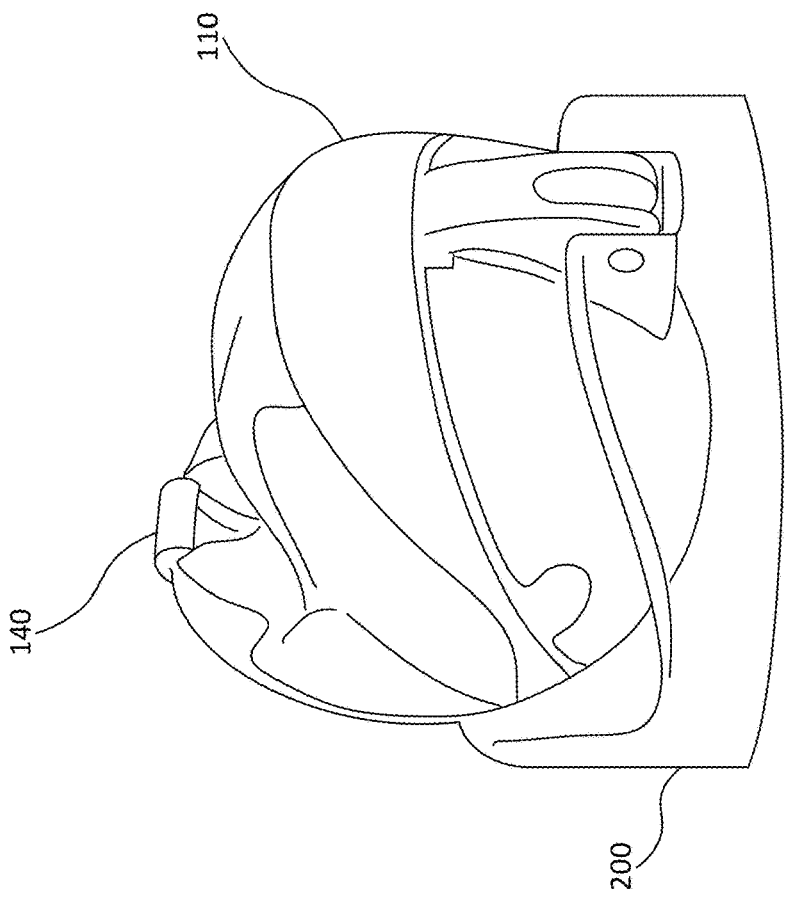
Figure 1F:
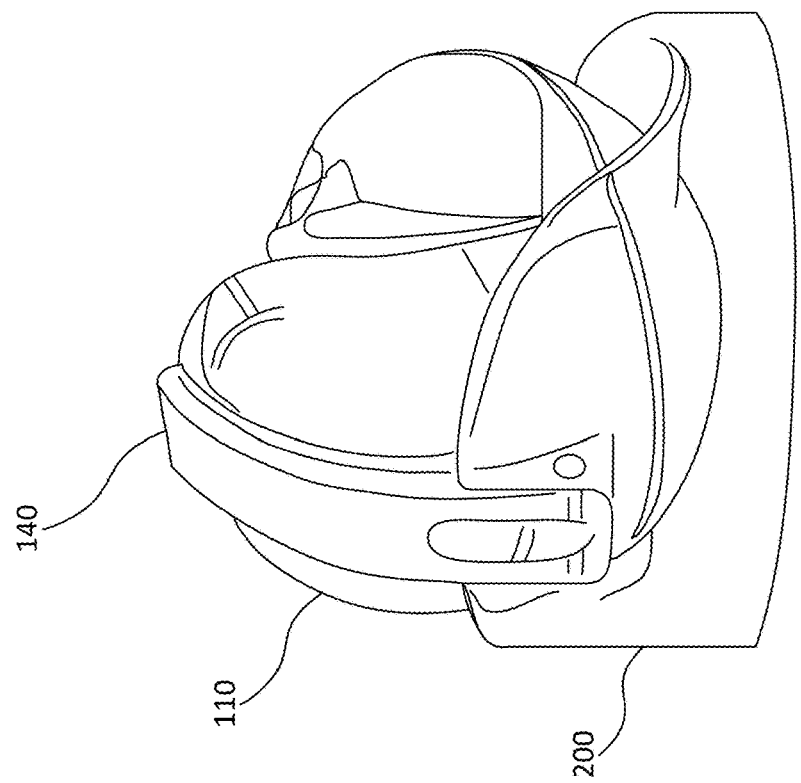
Figure 1G:
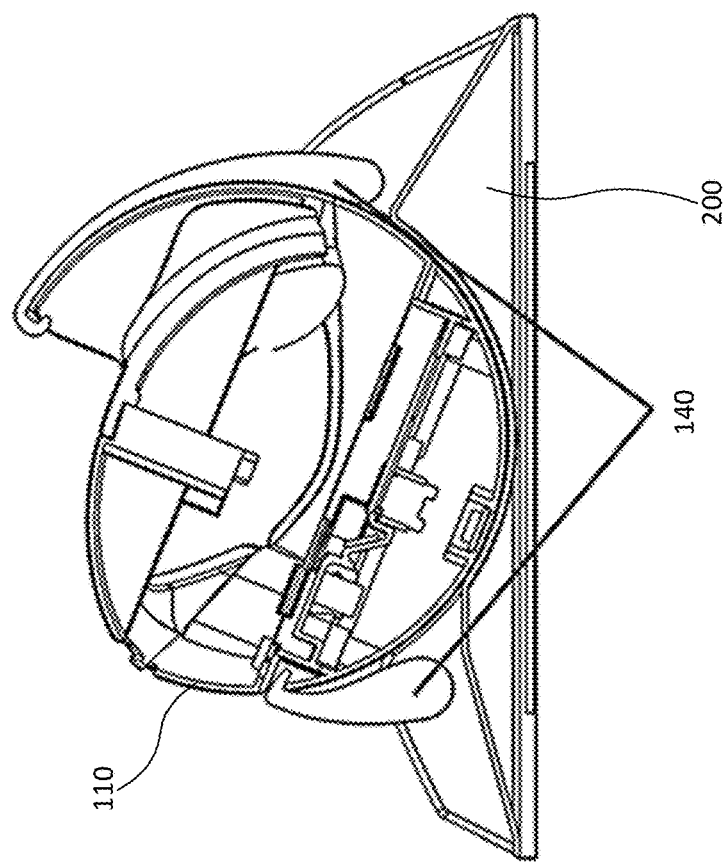
FIG. 1G shows a supplementary view of FIG. 1A.
Figure 1G:
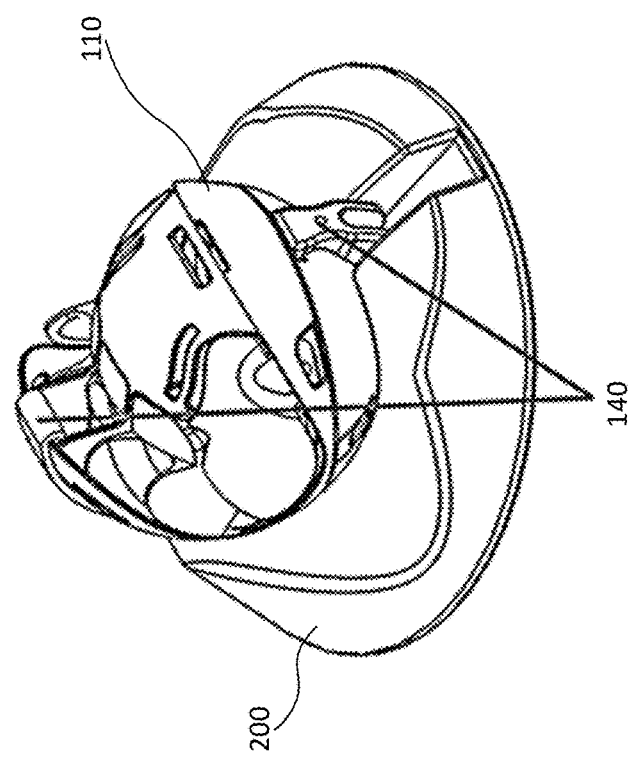
Figure 1H:
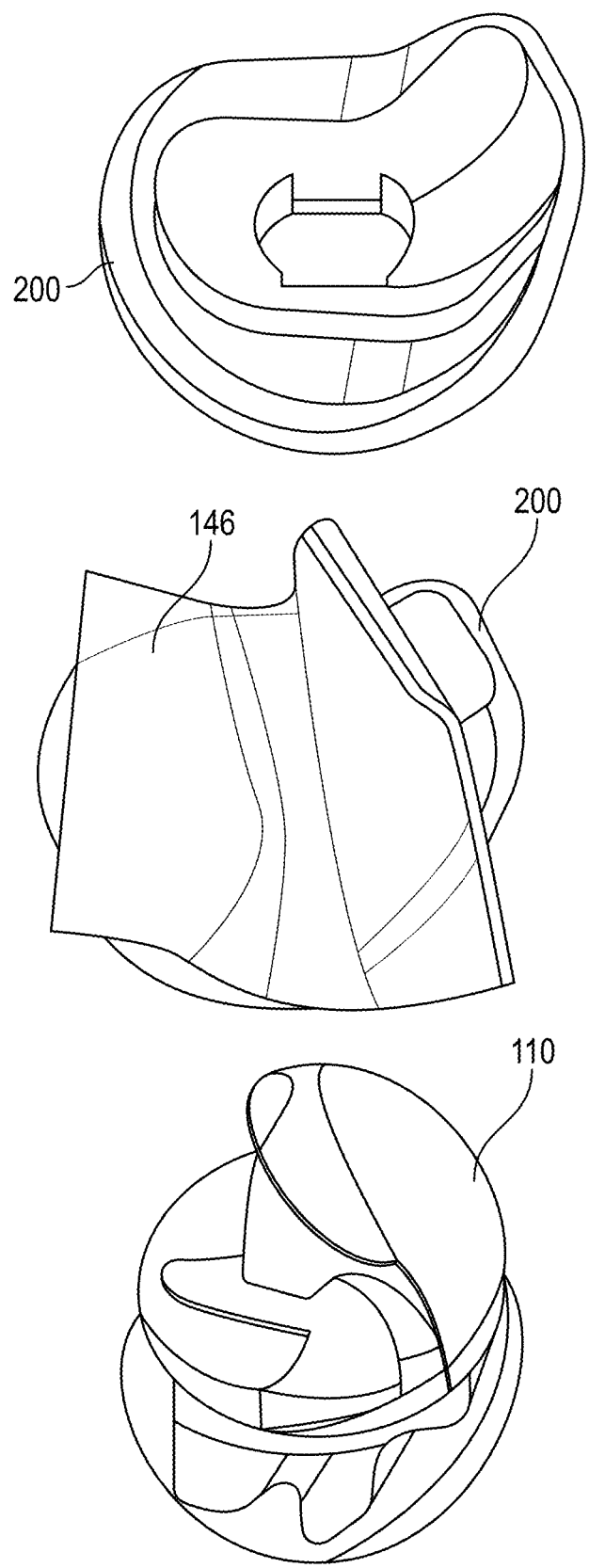
FIG. 1H shows a supplementary view of FIG. 1C.
Figure 1I:
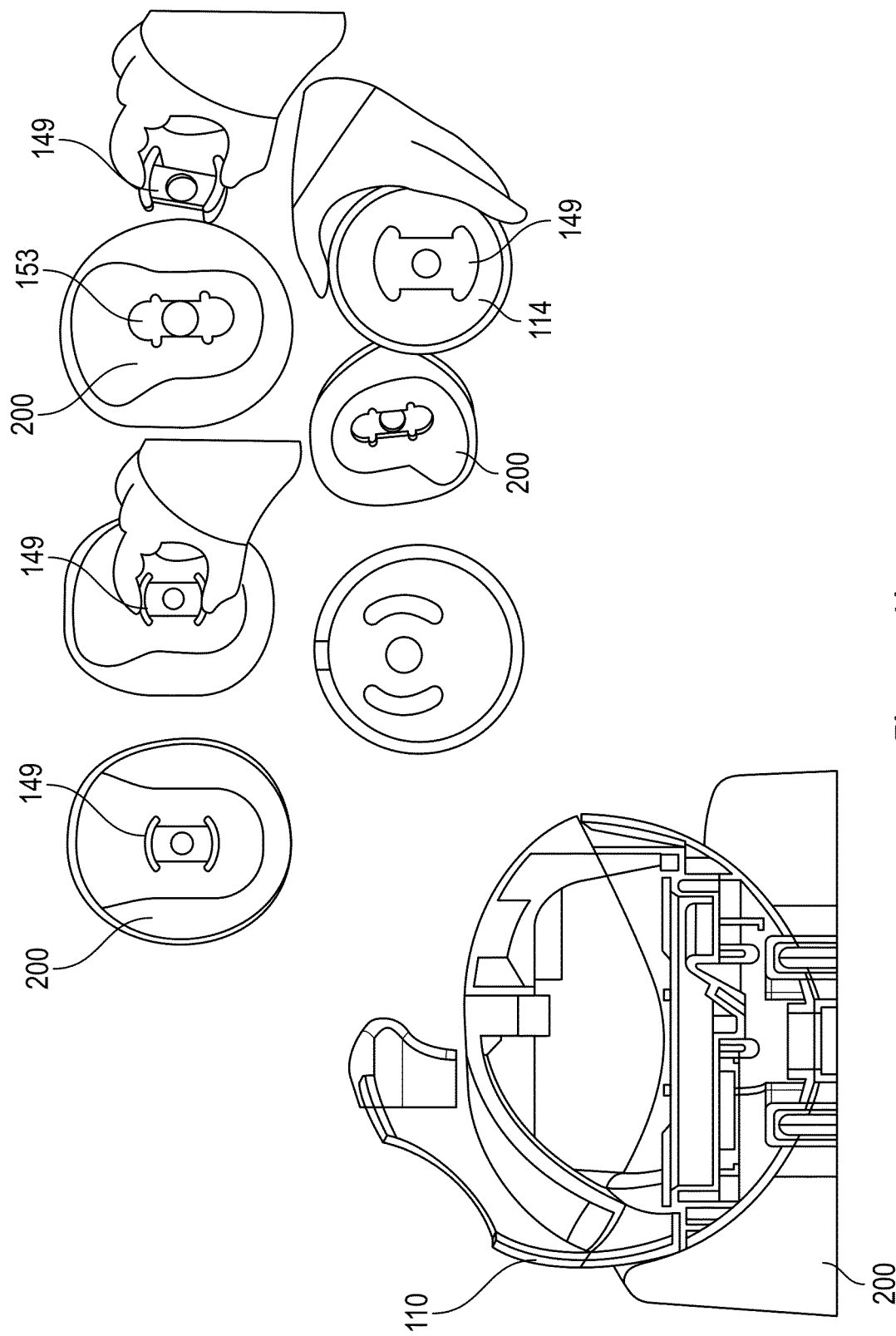
FIG. 1I shows a supplementary view of FIG. 1D.

FIG. 1I shows an embodiment, wherein a modular block 149 can be attached to the mounting 200 to fix the movement of the base 110 in order to reduce the difficulty of a user to affix their hand to the base 110. The modular block 149 may be surrounded by one or more specific recesses 153 designed to facilitate the removal and/or addition of the modular block 149. The lower hemisphere 114 of the base 110 can be similarly fitted with specific female recesses such that it fits together with the modular block 149. Optionally, the base 110 may be used with the modular block 149 directly on the working surface, without the mounting 200, such that the base 110 is operable to train different joints and muscles of the user's upper limb. That way the user can also train both their elbow (flexion/extension) and shoulder (internal/external rotation). When this training mode is used for rehabilitation purposes, the patient may be able to train movements required for activities of daily living, such as a "reaching" movement.

Figure 1J:
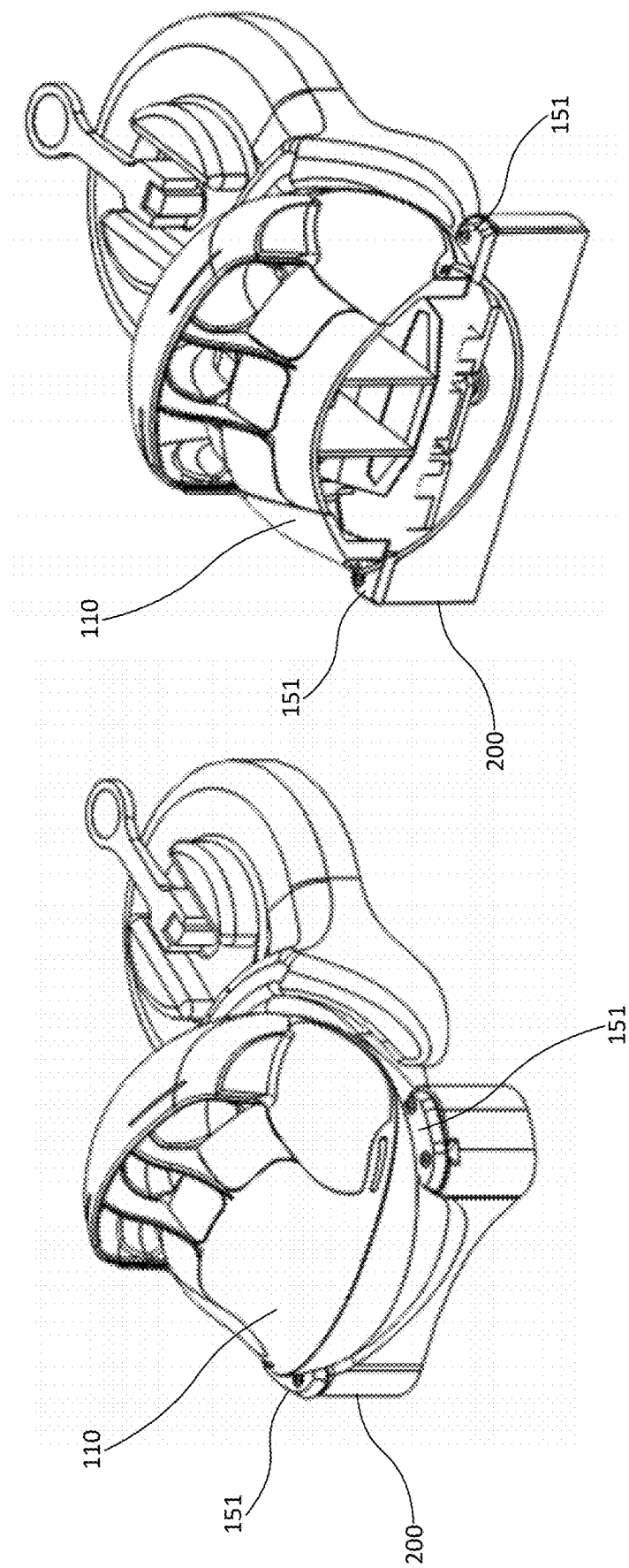
FIG. 1J shows a supplementary view of FIG. 1E.

The arrangement shown in FIGS. 1E and 1J comprises a pivoting system 151 wherein a lock installed on the mounting 200 is operable to pivot away from the base 110, thereby allowing the base 110 to rotate freely on the mounting. The same system can be used to lock the base 110 back to its original position.

FIGS. 1F and 1G show enlargements of the base locking mechanism of FIG. 1A. A hook 140 is provided on the base 110 or mounting 200 on either side. This arrangement provides a combination of stability, user friendliness and is the most cost-effective locking mechanism. A friction pad 146 may also be placed at the bottom of the mounting 200 for increased stability.

FIG. 1H shows a further view of the arrangement of FIG. 1C. In particular, the stages of assembly are shown when a friction pad 146 is used between the mounting 200 and the base 110. The mounting 200 is isolated from the base 110. The friction pad 146 is then placed on the mounting 200 such that it covers a portion of the mounting 200. The base 110 is then reintroduced to the mounting 200 wherein at least a portion of the friction mat 146 is in contact with both the base 110 and the mounting 200.

Figure 2A:
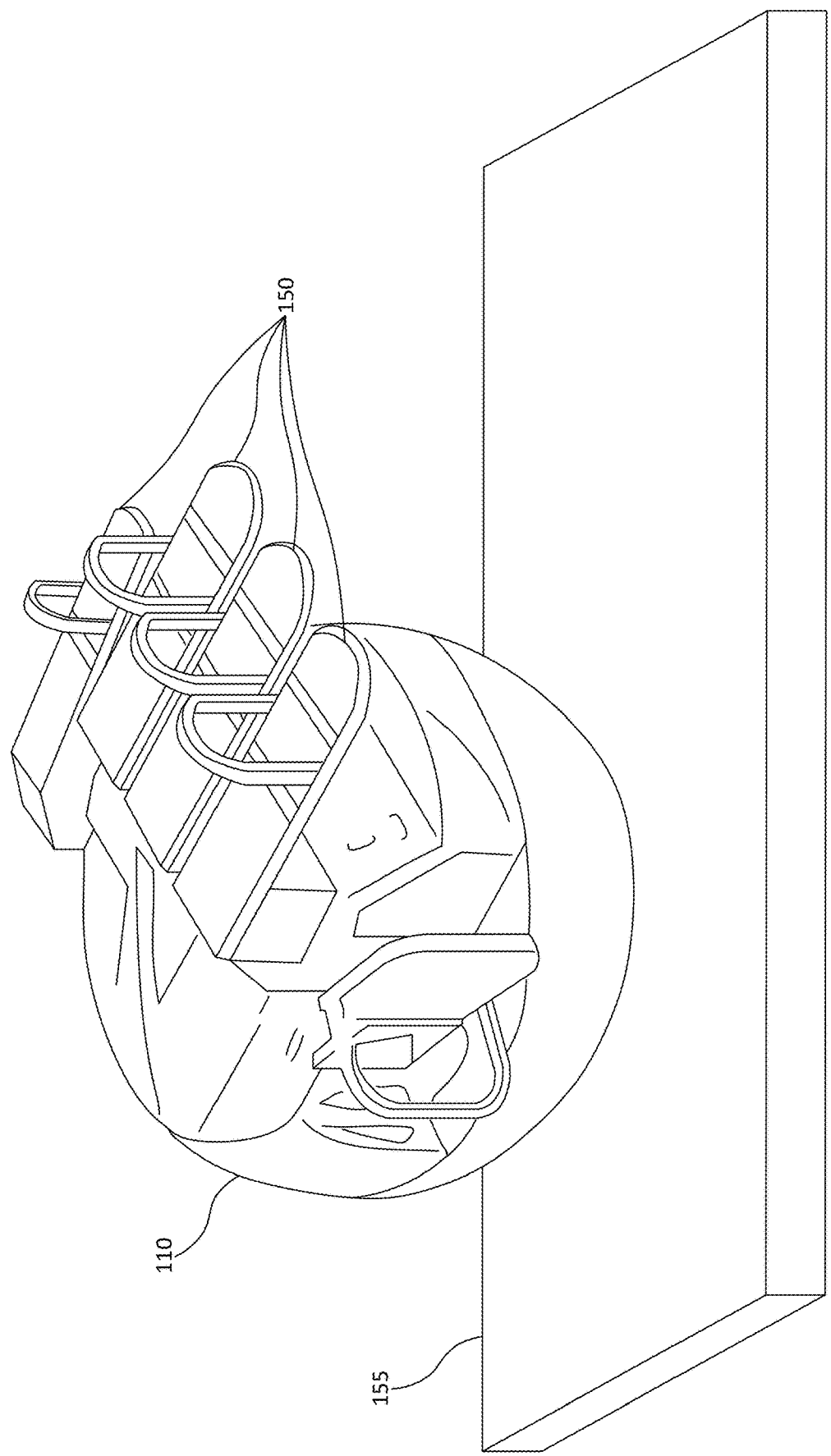
FIG. 2A shows a body of such an apparatus removed from a mounting.
Figure 2B:
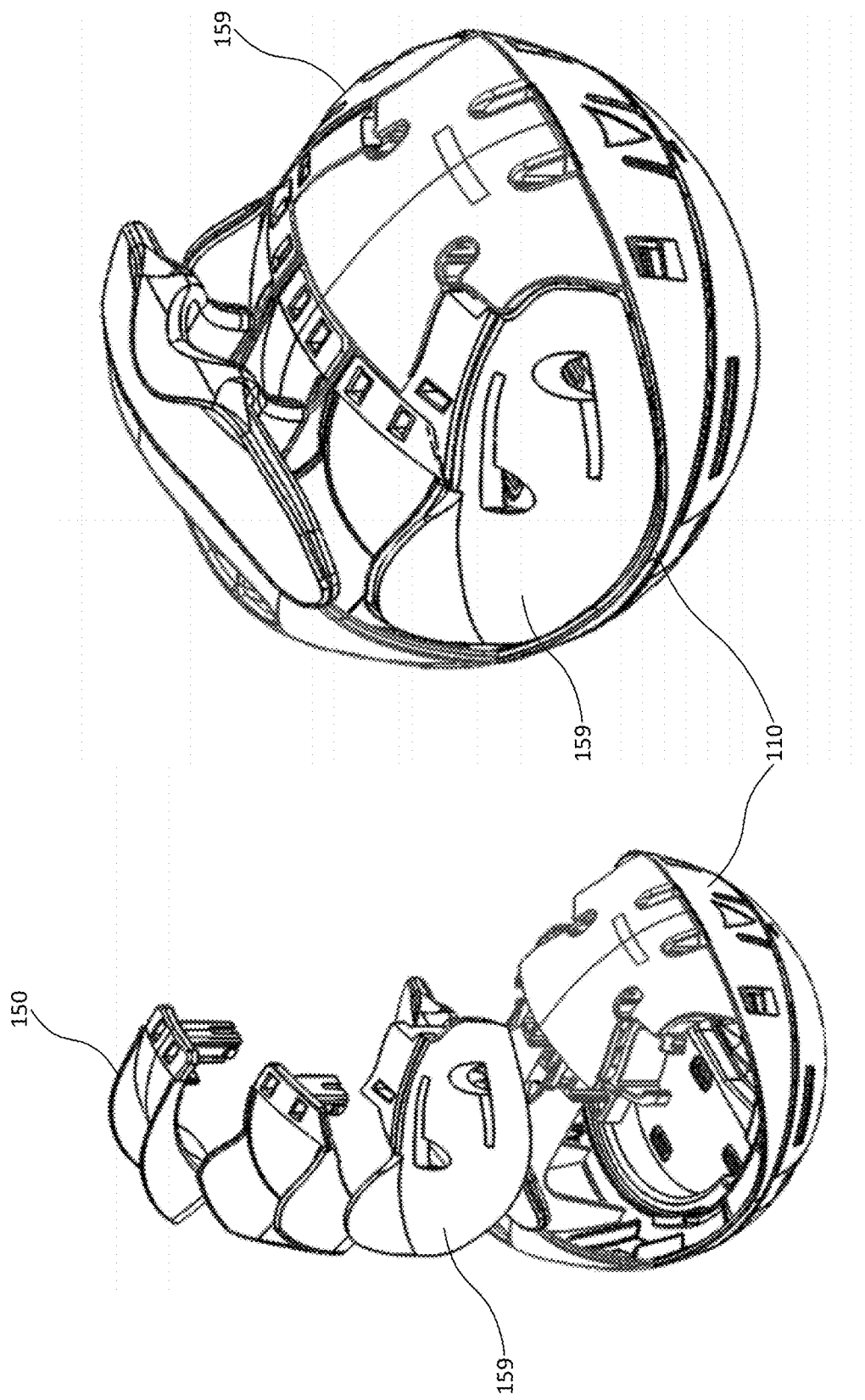
FIG. 2B shows an alternative embodiment of a body of such an apparatus removed from a mounting.

FIGS. 2A and 2B shows the body 110 removed from the mounting 200, with five finger supports 150 attached to the body 110 (the thumb is considered herein to be a "finger"). The thumb support 159 or the little finger support may be substituted for a button, in dependence upon the intended application of the apparatus 100. The body 110 may be used separately from the mounting 200, for example by being placed on a flat surface 155 (as shown in FIG. 2A), being placed on a user's legs or in a user's lap whilst the user is in a seated position, or being held in the user's hands. One or more of the finger supports 150 may comprise one or more holes for ventilation purposes (not shown). One or more of the finger supports 150 may be operable to detect and/or monitor a range of pressures applied by a user. The one or more finger supports 150 may be pressed more or less firmly, for example depending on the ability, training schedule, and needs of a user.

Figure 3A:
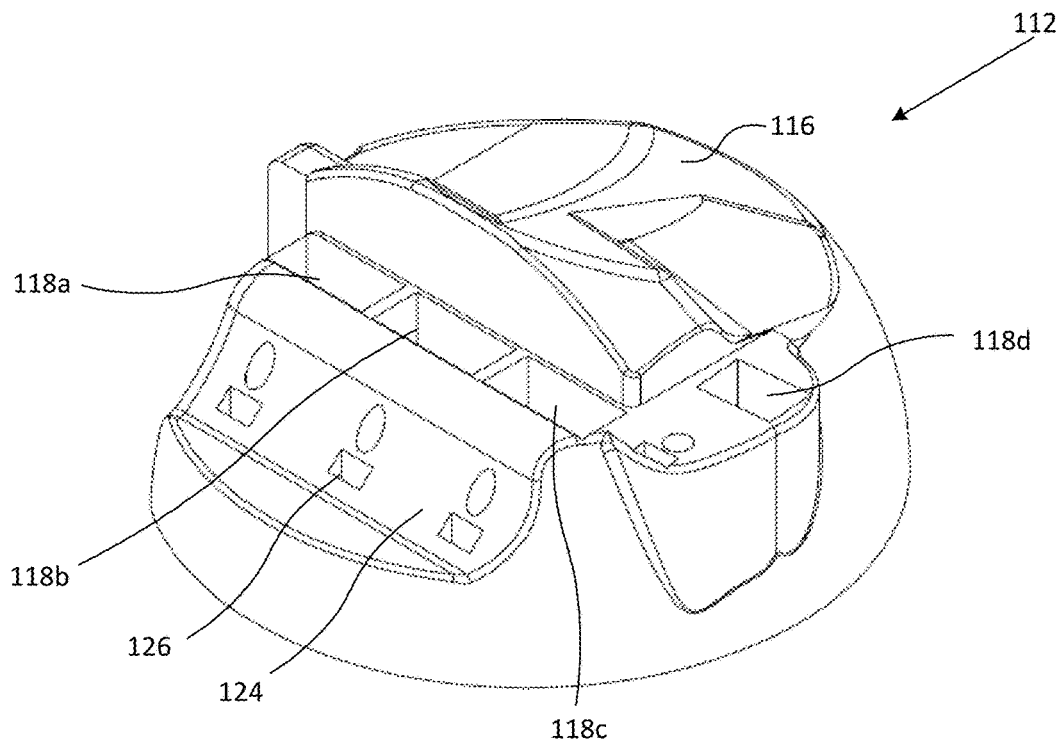
FIG. 3A shows a perspective view from above of an upper hemisphere of the body.

FIG. 3A shows a perspective view from above of the upper hemisphere 112 of the body 110. The upper hemisphere 112 comprises a flattened section 116 on an upper part of the upper hemisphere 112, to form a rest for the heel and/or palm of a user's hand. As such, the upper hemisphere 112 is not in fact a complete hemisphere. The flattened section 116 is shaped generally as a segment and extends from an outer edge to slightly over halfway through the upper hemisphere 112. The flattened section 116 curves upwardly away from the outer edge and downwardly towards one side thereby to correspond with the shape of a hand. In use, the flattened section 116 may serve to bring the user's wrist as close towards the centre of the body 110 (when viewed from above) as possible, as will be described later on.

A plurality of recesses 118 are provided proximate the flattened section 116 for mounting the finger supports 150. Three such recesses 118a, 118b, 118c (corresponding to the middle three fingers of the hand, the index finger, middle finger, and ring finger) are provided directly in front of the flattened section (in relation to a user's position during normal operation of the apparatus), while a further recess 118d (corresponding to the little finger) is arranged on the side of the flattened section 116 and behind the other three recesses. The origin of the little finger is a few centimetres closer to the wrist than the origin of the index, middle, and ring fingers. Placing the further recess 118d behind the other three recesses may provide more comfort and may also allow the training of the metacarpophalangeal ('MCP') and proximal interphalangeal ('PIP') joints of the little finger.

The recesses 118a-d extend downwardly towards the centre of the body 110, such that, when fitted, the finger supports 150 are slotted into the body 110 from above. It will be appreciated that, alternatively, the finger supports 150 may be slotted into the body from the right or left side. Additionally, the height of the finger supports 150, when fitted to the body 110, may be arranged so that the finger supports 150 are generally contiguous with the adjacent part of the flattened section 116.

A sloped section 124 is provided in front of the four recesses 118a-d, which provides space for finger supports 150 fitted to the recesses to be depressed into during use. The sloped section 124 may further comprise apertures 126 arranged in-line with the recesses 118 (and thereby in-line with the finger supports 150 fitted into the recesses 118) for holding sensors (not shown), as will be described later on.

Figure 3B:
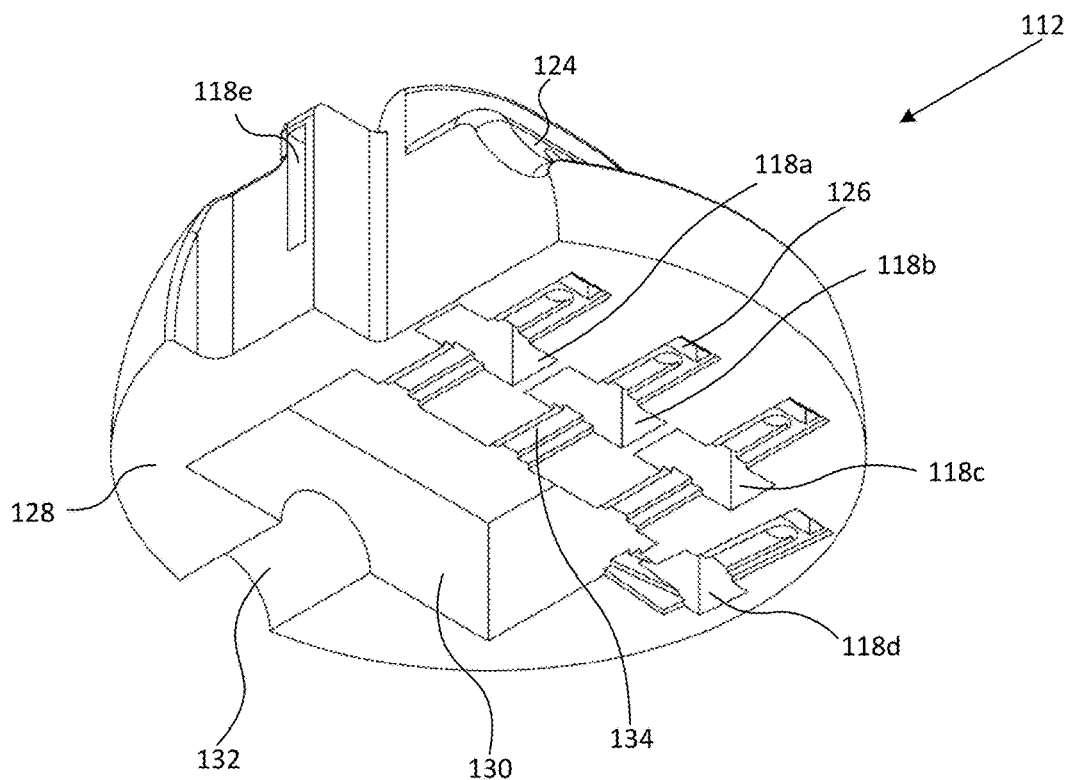
FIG. 3B shows a perspective view from below of the upper hemisphere of the body.

FIG. 3b shows a perspective view from below the upper hemisphere 112 of the body 110. The body 110 further comprises a thumb recess 118e, which is provided on a side of the upper hemisphere 112 opposite to the further recess 118d. The thumb recess 118e corresponds to the position of the thumb on the hand. The thumb recess 118e is arranged to be perpendicular in relation to the other recesses 118a-d, such that a finger support 150 fitted into the thumb recess 118e is arranged perpendicularly relative to finger supports 150 fitted into the other recesses 118a-d (though all of the finger supports 150 extend away from the body 110 generally in the same direction).

The further (e.g. little finger) recess 118d and the thumb recess 118e may be of different sizes to the other three recesses 118a-c as a consequence of the thumb and little finger being of different dimensions to the index, middle, and ring fingers. It may also be necessary for the recesses 118*d* and 118*e* to be of different sizes owing to the limited space available within the upper hemisphere 112, meaning that different finger supports 150 are used with different recesses 118 (although the finger supports 150 for use with the middle three recesses 118*a-c* are interchangeable). It will be appreciated that all of the recesses 118 may of course alternatively each have the same size, thereby allowing the interchangeable use of the same size of finger support 150 with all of the recesses 118.

A generally rectangular cavity 130 is provided on a flat lower surface 128 of the upper hemisphere 112. The flat lower surface 128 is arranged to abut a corresponding flat surface of the lower hemisphere 114 (having a corresponding cavity) thereby to form the body 110. The outer edges (e.g. the perimeter) of the cavity 130 are arranged to align with the outer edges of the corresponding cavity provided in the lower hemisphere 114, thereby to provide a larger cavity for housing processing and sensing components, as will be described later on.

A generally semi-circular cut-out 132 is provided on one side of the cavity 130 (opposite the side adjacent the central three recesses 118*a-c*), which is arranged to align with a similar cut-out on the lower hemisphere 114 thereby to create a circular aperture in the body 110, thereby to allow a data connection and/or power connection to be connected to the components housed within the cavity 130 from outside the body 110.

The recesses 118*a-d* extend through the upper hemisphere to the flat surface 128. A plurality of recessed slots 134 are provided on the flat surface 128, which extend between the cavity 130 and the recesses 118, thereby to allow a wire (or other connection) to extend between the cavity 130 and the recesses 118. The recessed slots 134 also extend up to the apertures 126 in the sloped surface 124, which extend through to the flat surface 128.

Figure 4:
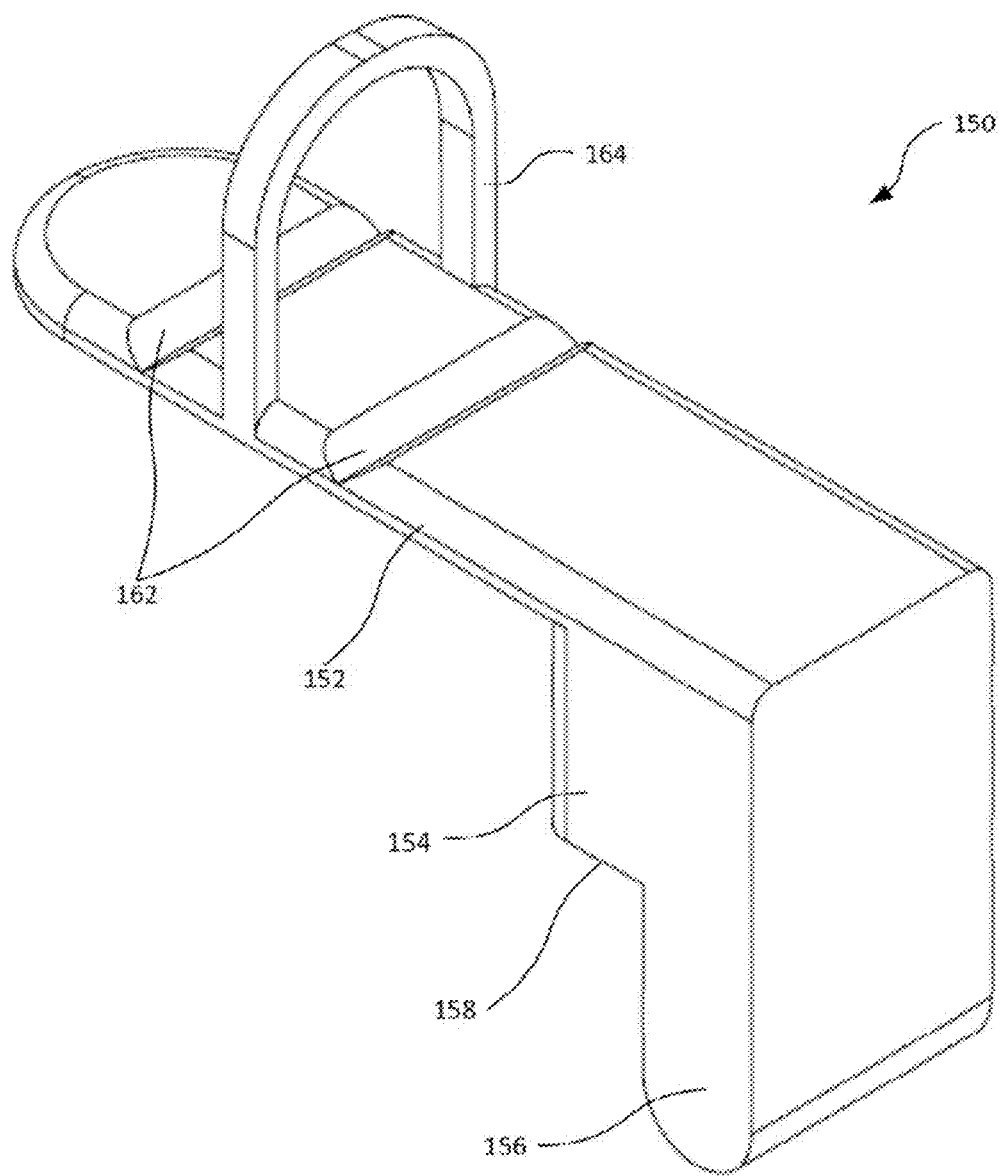
FIG. 4 shows a finger support of the apparatus.

FIG. 4 shows a finger support 150 in detail. The finger support 150 comprises a support portion 152 and an attachment portion 154. The attachment portion 154 is arranged at a proximal end of the support portion 152 (in relation to a user's hand). The attachment portion 154 has a projecting portion 156 arranged to fit inside a recess 118 of the body 110 to (removably) attach the finger support 150 to the body 110. Where the projecting portion 156 extends out from the attachment portion 154, a shoulder 158 is formed upon which the finger support 150 rests when fitted to the body 110.

The support portion 152 is arranged generally perpendicular to the attachment portion 154 when attached, such the support portion 152 extends away from the body 110 when the base is fitted into a recess 118. The support portion 152 is elongate and relatively thin, such that it can deform (or deflect) under pressure from a user's finger. It is to be appreciated that the support portion 152 could also be relatively thick, to provide more stiffness and requiring more pressure from a user's finger to deform or deflect. The support portion 152 is rounded at a distal end, thereby to mimic the shape of a user's finger and to avoid sharp edges. Two or more joints 162 are provided on the support portion 152, the joints 162 being relatively thinner than the remainder of the support portion 152 to enable bending of the finger support 150. It is also envisaged that the support member 150 may have a variable stiffness. In use, the finger support 150 deforms by the support portion 152 bending at the joints under pressure from a user's finger. The joints 162 are positioned so as to mimic the joints of a user's finger.

The support portion 152 further comprises a support loop 164 for retaining a user's finger on the finger support 150. The support loop 164 may extend above the upper surface of the support portion 152.

At least the support portion 152 of the finger support 150 is formed from a resilient material, thereby to resist any movement of the support portion 152 away from an initial (neutral) position (i.e. the position in which the support portion 152 extends at 90 degrees to the attachment portion 154). This may allow a user to train a functional grasping motion using the apparatus 100. The finger supports 150 can move independently relative to the body 110, which may improve training due to the ability of each of the user's fingers being able to be trained independently.

The stiffness of the support portion 152 is arranged so as to assist hand release (i.e. opening a hand of a user suffering from spasticity of the hand and/or fingers, in particular users whose fingers form a closed fist), either in assisting the user to keep their hand open or in assisting in opening the hand when it is closed. It will be appreciated that the removable and modular nature of the finger supports 150 allows various different finger support configurations to be used with the apparatus 100 depending on a user's requirements. In particular, the stiffness of the support portion 152 may be selected in dependence on the severity of the user's spasticity and/or the user's grip strength. Furthermore, the size (for example, the length and width) of the finger supports 150 may be selected in dependence on the size and/or dimensions of the user's fingers.

In order for users suffering from spasticity to put their hand on the apparatus 100, they can flex their wrist, potentially with the assistance of their non-paretic hand, causing their fingers to loosen and hang below their hand. The hand and fingers may then be guided onto the apparatus 100, where the apparatus 100 is stabilised on the mounting 200 (as described in connection with FIG. 5 and FIGS. 1A to 1J) or held (for example, in the non-paretic hand) such that the finger supports 150 are generally parallel with the fingers. It is envisaged that the apparatus 100 may be stabilised on the mounting 200 (as described below in connection with FIG. 5 and FIGS. 1C to 1J) either in its resting position or rotated at approximately either 45 or 90 degrees if this provides extra help to a user when placing their hand on the device. It is envisaged that the apparatus 100 may also be stabilised between the legs of a user. The finger support loops 164 on each finger support 150 may then provide assistance for guiding a user's fingers into the correct position. The finger support loops 164 may be formed as part of a different part of the apparatus 100, and this is discussed in more detail below. The finger supports are provided in order to separate the fingers and guide the fingers of a user into the apparatus 100.

Alternatively, the body 110 may be supported in the mounting 200, and the user may open the closed first of their paretic hand with their non-paretic hand, or with the help of a third person. The palm and/or heel of the paretic hand may then be placed on the flattened section 116, and the user's fingers may be guided through the finger support loops 164.

Figure 5:
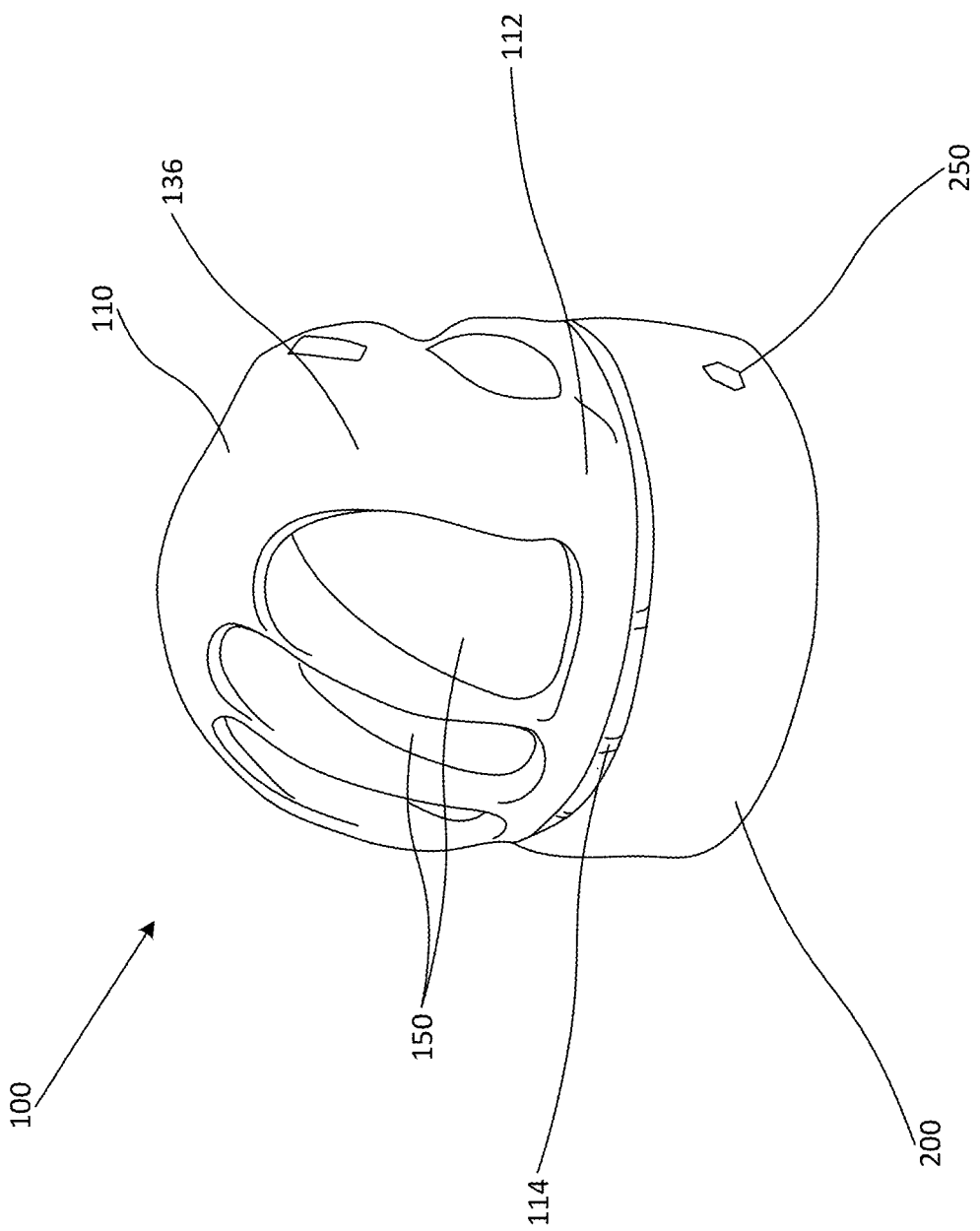
FIG. 5 shows a view of a body according to another aspect of the present invention.

FIG. 5 shows an apparatus 100 according to a second aspect of the present invention with the body 110 placed within a mounting 200. The body 110 has a guide 136 for a user's fingers. The guide 136 may comprise openings provided on the upper hemisphere 112, to assist a user in placing their fingers into the apparatus 100, and the guide 136 extends out from the surface of the upper hemisphere 112. The guide 136 has discrete openings to accommodate a user's fingers. The body 110 may be supported at approximate 90 degrees to its normal position as the user directs their fingers of their paretic hand though the openings of the guide 136, and then rotated to its normal position by a user.

The user may separate each finger from their partially or fully closed first and guide one finger each time inside through the openings into the finger support. In order to improve the ease with which a user may guide their fingers through the openings into the finger support, the body 110 of the apparatus 100 may be stabilised on the mounting 200. Such stabilisation may employ one or more pins as described herein passed through the apertures 250 in the mounting 200 and into corresponding apertures (not shown) in the body 110.

These pins lock or secure the body 110 in a non-moveable configuration such that the apparatus 100 is stabilised on the mounting 200. Once the user's hand is placed through the guide 136 and their fingers are within the body 110, the pins may be removed from the apertures 250, such that the body 110 may then be moved with respect to the mounting 200.

The discrete openings in the guide 136, formed out of rigid or semi-rigid material may enable the user to place their hand within the body 110 more easily than using one or more loops formed of a soft material which deform if the user's hand is pressed into them.

If the loops are deformable, placing a hand within the body 110 may be more difficult for a user.

It will be appreciated that the aforementioned arrangement of the finger supports 150 on the body 110 may allow the user to easily place their fingers on the finger supports 150 and to keep their fingers in place comfortably. This may also allow the apparatus 100 to be used by the user independently (i.e. without any help to put their hand on the device, and without any help to train using the device). It will be further appreciated that the generally spherical shape of the body 110 provides an ergonomic advantage in that it adds to a user's comfort and makes it easier for a user to grip the apparatus 100. It has been found that a generally cylindrically-shaped body 110 may also provide an ergonomic and comfortable solution, but it may be preferable to use a spherical shape in order to provide a finger opening mechanism and the control circuitry (described below) within the apparatus 100. A spherical shape may also enable an apparatus 100 with improved aesthetics, as compared to a cylinder-liked device.

Figure 6:
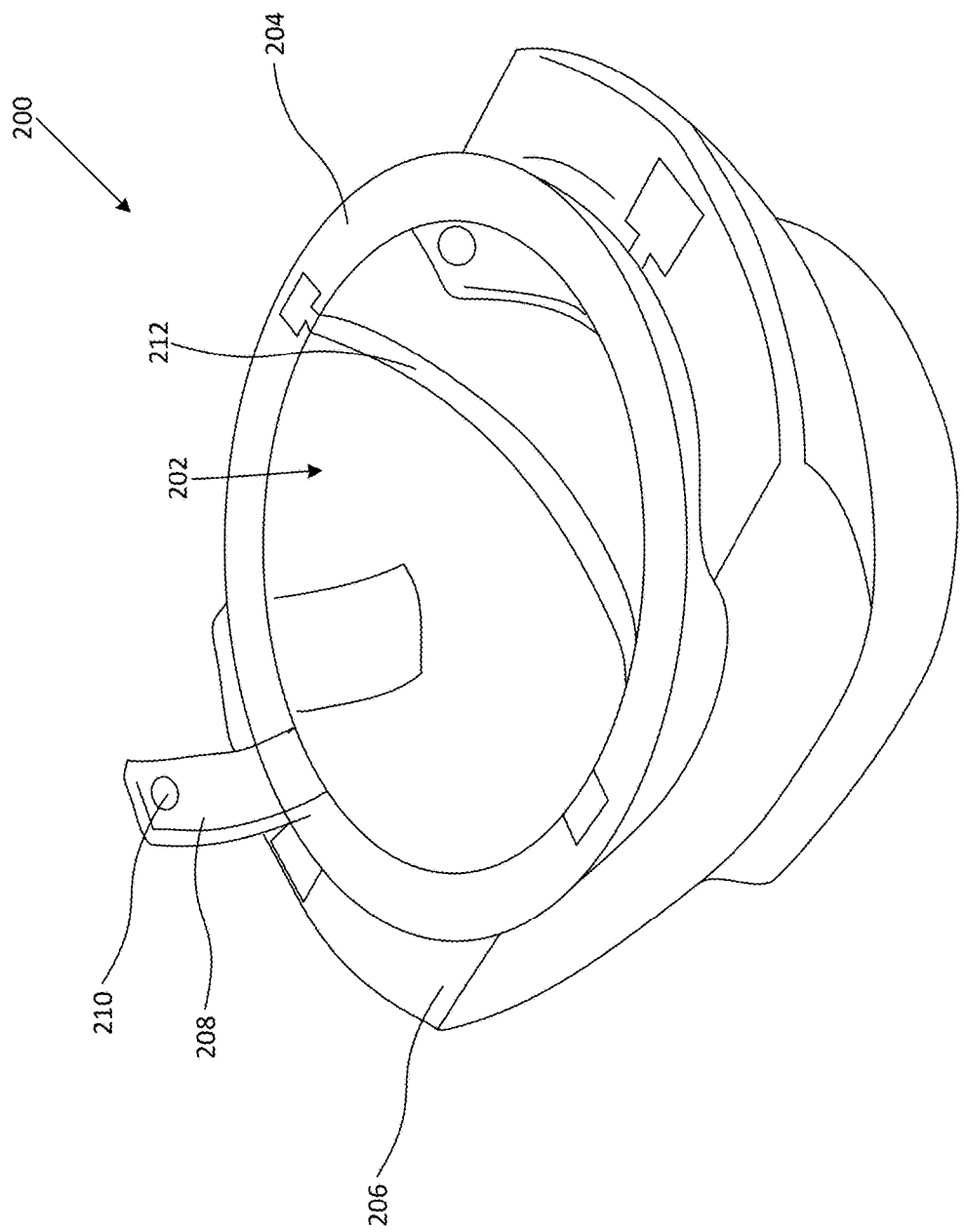
FIG. 6 shows a view of the mounting.

FIG. 6 shows a view of the mounting 200 of the apparatus 100 according to the second aspect. The mounting 200 comprises a generally bowl-shaped inner portion 204 having a recess 202 for supporting the body 110, and a generally bowl-shaped outer portion 206, where the inner portion 204 rests within the outer portion 206. The inner portion 204 comprises a pair of arms 208 extending away from the inner portion 204, where the arms 208 comprise holes 210 at a distal end from the inner portion 204. The arms 208 are arranged to engage with the body 110 so as to retain it, for example by way of a friction fit (or other connection). This engagement allows the body 110 to rotate about the axis of the holes 210. The inner portion 204 further comprises a supplementary groove 212 running along the central axis of the inner portion 204, generally perpendicular to the axis of the holes 210. The supplementary groove 212 may be used to engage with a formation (not shown) provided on the underside of the body 110, thereby to provide additional support during rotation, and the supplementary groove 212 may be used to add resistance to the movement of the body 110 with respect to the mounting 200. This may be achieved by placing springs (not shown) within the supplementary groove 212. Such springs may be used to bias the position of the body 110 in a particular orientation with respect to the mounting 200, or may resist the movement of the body 110 with respect to the mounting 200 in order to make movement of the body more difficult.

The arms 208 further serve to allow the body 110 to be connected to the mounting 200 via a "snap fit" between the aperture 210 and corresponding components on the body. The stiffness of the arms 208 is arranged so as to allow an easy and stable fit. The body 110 is arranged to fit into the arms 208 with an audible 'click', thereby to assist users having poor vision.

As previously mentioned, the body 110 is arranged to pivot in relation to the mounting 200 (allowing the movement of the user's wrist to be trained) by rotating within the recess 202 for supporting the body 110. The body 110 may rotate about up to 3 orthogonal axes of rotation (i.e. the body has three degrees of freedom)—when the side of the body which the finger supports 150 extend out in front of is considered to be the "front" of the apparatus, these may be referred to as "roll", "pitch", and "yaw", or alternatively rotations around one or more of the x, y, and z axes. In use, these axes respectively correspond to three wrist movements (which are referred to as "pairs", relating to each direction of the motion): pronation and supination of the forearm, flexion and extension of the wrist, and abduction and adduction (which may also be referred to as ulnar deviation and radial deviation) of the wrist.

In use, the heel and/or palm of the user's hand is supported on the flattened section 116 of the upper hemisphere 112 such that the user's wrist is close to one or more of the axes of rotation. This reduces the involvement of the shoulder in the case that the training is intended to focus on the user's wrist. Shoulder contribution to movement training may cause pain and fatigue to a user's shoulder.

It is envisaged that a user's wrist joint may be located at the intersection point of the three degrees of freedom of the apparatus 100. With an increase in distance between the user's wrist and the intersection point of the three degrees of freedom, the more a user's upper arm and shoulder must contribute to rotation of their wrist. The apparatus 100 may therefore position the user's wrist at a relatively small distance from the intersection point of the three degrees of freedom in order to reduce the contribution of their upper arm and shoulder to rotation of their wrist, in case this is required.

Figure 7:
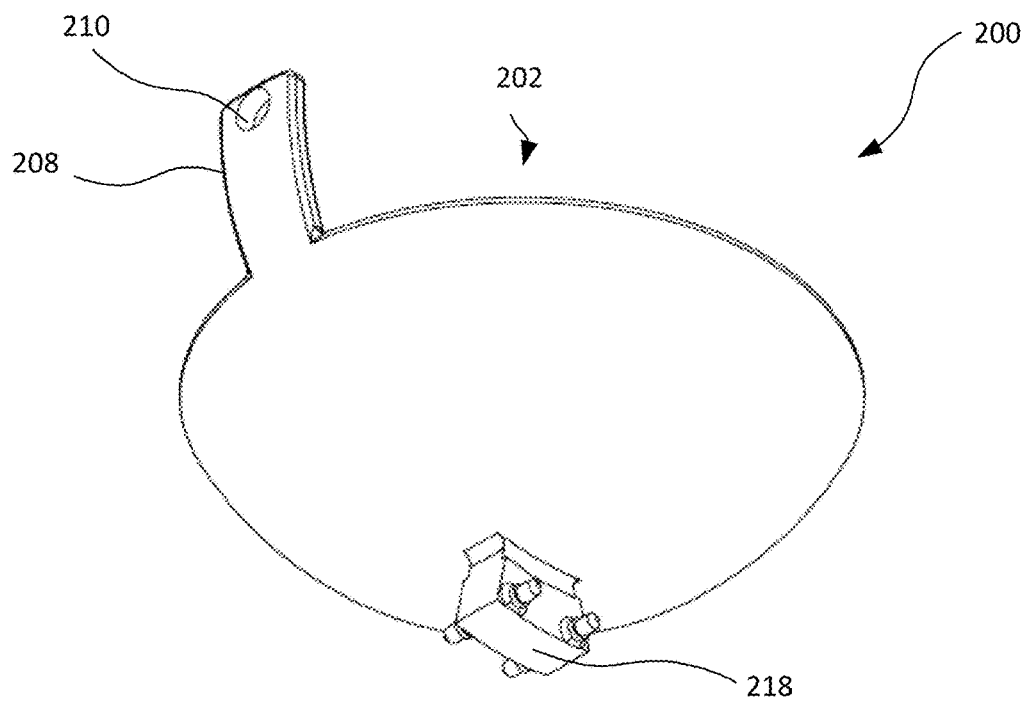
FIG. 7 shows an exploded view of the mounting.
Figure 7:
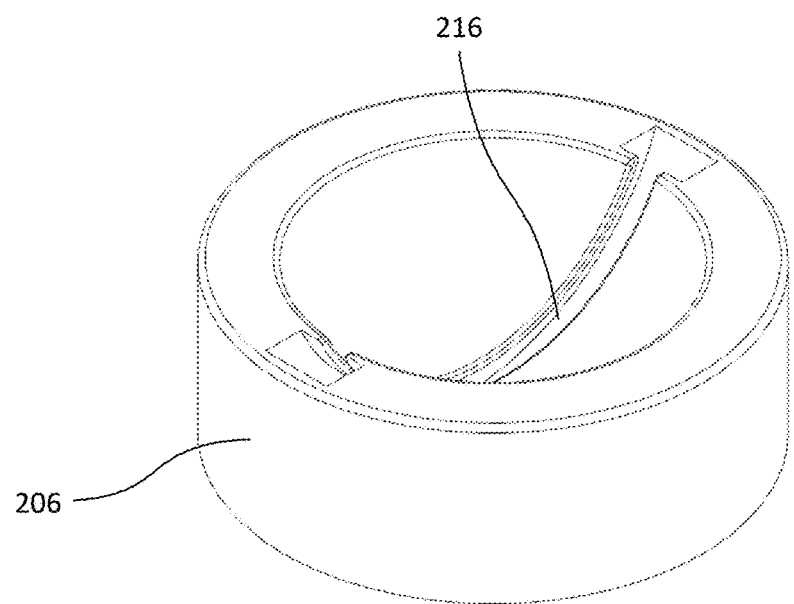

FIG. 7 shows an exploded view of the mounting 200 of FIG. 6. The outer portion 206 comprises a further groove 216 (also shown in FIG. 6) which may accommodate a formation 218 on the underside of the inner portion 204. The further groove 216 may allow the inner portion 204 of the mounting 200 (which is attached to the ball) to "roll" relative to the mounting 200.

To clarify, the groove 212 may allow the body 110 to move with respect to the mounting 200, to allow "pitch" of the body 110, while the groove 216 may allow to the inner portion of the mounting to move relative to the outer portion of the mounting, to allow "roll" of the body 110.

The apparatus 100 allows "pitch" (which causes wrist flexion and extension) by moving relative to the mounting, specifically by being connected to the apertures 210 of the inner portion.

The apparatus 100 allows "roll" (which causes forearm pronation and supination) by way of the further groove 216, which allows the relative movement of the inner portion 204 (attached to the apparatus 100) with respect to the outer portion 206.

The alternative groove 216 is arranged to engage with the formation, thereby to retain the inner portion 204 within the outer portion 206 and to allow the inner portion 204 to rotate relative to the outer portion 206. The body 110 can thereby rotate relative to the mounting about two orthogonal axes (i.e. about the axis defined by the apertures 210 in the arms 208, and about the axis defined by the rotation of the inner portion relative to the outer portion). Although not shown in FIG. 7, a third axis of rotation may also be provided, for example by mounting the formation to the inner portion such that it can swivel.

Each of the grooves 212, 216 may include springs or elastic material (not shown) internal to the groove. The springs can be set up to either assist or resist the user's rotation of the body 110 in a particular direction, in dependence on the user's particular requirements.

The apparatus 100 may resist to "pitch" movement if springs or the like are included in the groove 216, as stated above. The apparatus 100 may resist "roll", if springs or the like in the groove 216, similarly to the groove 212.

By allowing the body 110 to rotate freely relative to the mounting about two or more axes, preferably all three axes (i.e. such that the body and the mounting generally form a ball joint), the user can perform a combination of the three aforementioned movements—forearm pronation/supination, wrist flexion/extension, and wrist ulnar and radial deviation). However, training one of the wrist movements alone (which is typically desired in stroke rehabilitation physiotherapy) can be difficult for some users in a 'free rotation' mode due to instability, muscle weakness, and a tendency to compensate by using other movements in combination with the movement to be trained. This may necessitate the use of any appropriate arm support which may minimise movement contribution by the user's shoulder.

In the apparatus 100, the pivoting of the body 110 about two or more axes can be selectively restricted (or "constrained"), such that the body 110 can only pivot about a reduced number of axes (i.e. such that the body can only rotate about one axis or about two axes). Motion can be constrained by the insertion of a mechanical block into the grooves 212, 216, for example, or alternatively/additionally by the use of magnets and/or gears. The number of degrees of freedom of the apparatus 110 can be selected and manually configured by the user, for example by pressing a button to lock or rotating a part of the mounting 200 to lock a component in place. Allowing the pivoting of the body 110 to be constrained may provide for improved training for less able users. The constraints can then be removed as the user becomes more able and/or recovers motor function. This functionality may enable the training of 'pure' movements, that is to say one movement of an arm or wrist at a time. By way of an example, it may be desirous to train only wrist flexion and/or extension in a user. If the apparatus 100 enabled movement in all three degrees of freedom, a user would need to have good control of their movement in order to carry out 'pure' flexion and/or extension. It has been found to be the case that those recovering or being rehabilitated after a stroke or the like have unstable movement, find it difficult to control their arms. The apparatus 100 may be configurable in order to allow unrestrained movement (that is to say in three degrees of freedom), or constrained movement (which may be in only one degree of freedom) in order to provide versatile training.

It will be appreciated that there are many possible mechanisms that could be used to allow the body 110 to be rotated with various degrees of freedom, and to allow the said degrees of freedom to be restricted/constrained as necessary.

Figure 8:
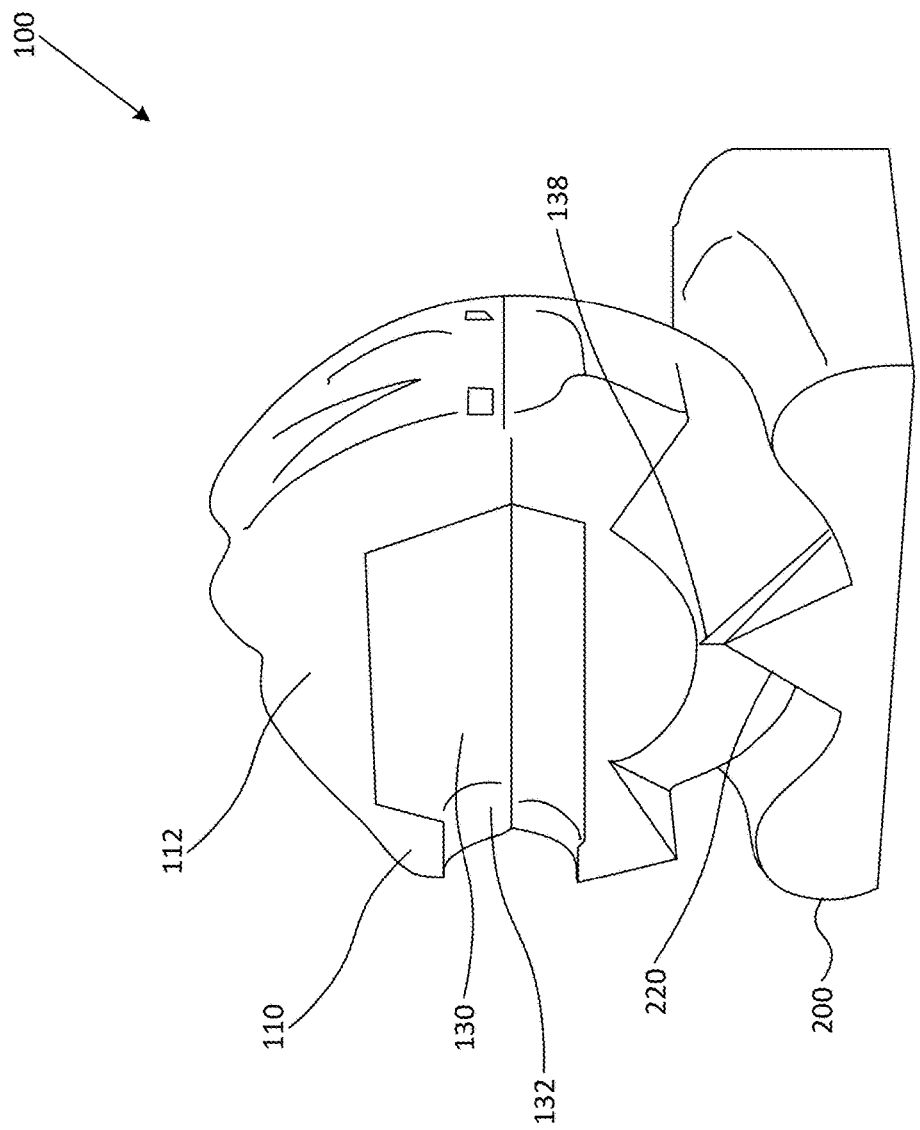
FIG. 8 shows a cutaway schematic view of alternative apparatus.

FIG. 8 shows a cutaway schematic view of the apparatus 100 of the second aspect, showing an alternative attachment mechanism between the body 110 and the mounting 200. The mounting 200 comprises a formation 220 in the centre of the recess 202, where the formation is shaped generally as a square pyramid, although it is to be appreciated that other shapes may be used. The lower hemisphere 114 of the body 110 is provided with a pair of overlapping grooves 138, the edges of which are arranged to abut the formation when the body is in situ in the recess. Since the grooves 138 overlap, the body can pivot relative to the mounting about either one axes or another, thereby allowing constrained training. Optionally, either the body 110 or mounting 200 is arranged to be modular, such that it can be swapped with another such body/mounting having differently shaped groove or a differently shaped formation, thereby to vary the number of degrees of freedom. For example, providing only one groove in the body 110 allows for only one degree of freedom, while providing a generally conic region in place of the overlapping grooves allows for generally free rotation.

In the case that the formation 200 in the recess 202 of the mounting 200 is of a generally pyramidal profile and the body 110 includes two overlapping grooves 138 in the lower hemisphere 114 thereof, the body 110 may only be moved in one degree of freedom which, for example, may allow training of wrist flexion/extension. If the mounting 200 is then rotated through 90° with respect to the body 110, movement of the body 110 with respect to the mounting 200 may still be constrained to one degree of freedom, but in a different direction. This may, for example, may allow training of forearm pronation/supination.

It will be appreciated that in a 'free rotation' mode the mounting 200 is not required, as the body 110 can simply be placed on a flat surface. However, the use of the mounting provides more stability, which may increase the quality of the wrist training delivered and may also make it more suitable for less able users.

It will further be appreciated that the apparatus 100 allows for simultaneous or selective finger and wrist training, and that the variety of modes and modularity available allow for flexibility in training depending on a user's needs and desires. Furthermore, detaching the body 110 from the mounting 200 allows for the elbow and shoulder to be trained—for example, functional reaching and grasping movements can be trained by supporting the body 110 with the non-paretic hand, reaching forwards with both hands, and manipulating the finger supports 150 as described.

The apparatus 100 further comprises a variety of sensors for quantifying the user's interaction with the device. In particular, force sensors, for example capacitive force sensors or force sensitive resistors, ('FSRs') may be used to quantify the force exerted by the user on the finger supports 150, and flex sensors (such as capacitive flex sensors) are used to quantify the displacement of the finger supports 150. FSRs and flex sensors are provided on, or internally, to the members 152, and may be arranged to communicate with control circuitry located in the cavity 130. Certain sensors may optionally be provided in the apertures 126 on the upper hemisphere 112. Proximity sensors may be used in combination with or in place of the force sensors discussed above. These may include optical sensors, infrared sensors, ultrasonic sensors, or hall effect sensors, and these sensors may measure the displacement of the finger supports 150 by measuring the initial and final positions of the finger supports 150 or the joints 162, and this displacement may be used to determine the force applied to the finger supports

150. The spring stiffness of the finger supports 150 may be used, in combination with the displacement, to determine the force applied.

Further, the finger supports 150 may include vibration sources or other tactile feedback arrangements in order to provide tactile feedback and provide sensory learning after a stroke.

The body 110 further comprises an inertial measurement unit (IMU), which is provided in the cavity 130 adjacent to (and in communication with) the control circuitry. The IMU comprises a magnetometer, an accelerometer, and a gyroscope, and is used to detect changes in orientation of the body that occur as the body is rotated (when mounted to the mounting, or otherwise). The control circuitry is arranged to transmit data, and such transmission may be through a wire running through the aperture formed by the cut-out 132 to a computing device, such as a personal computer, tablet computer, television or smartphone. Alternatively, a wireless data connection may be used. This may be, for example, by way of Bluetooth communication or alternatively via a Wi-Fi connection. It is envisaged that the apparatus 100 may be connected to a virtual reality ('VR') or augmented reality ('AR') platform, and such a connection may be achieved by one of the connection methods detailed above. Such a connection may alternatively be achieved by way of an alternative communication arrangement.

The apparatus 100 may include optical-acoustic arrangements which may be light sources, for example LEDs, and/or audio or sound sources, for example speakers or sound transducers. The light sources may be positioned in the finger supports 150, and the audio or sound sources may be positioned within the apparatus 100.

These optical-acoustic arrangements may be used to guide a user through training which is independent of a connection to a computing device. The apparatus may be configured to illuminate a light source in a finger support 150, with the audio or sound source configured to provide an instruction to the user which may instruct them to press the lit finger support 150. The apparatus 100 may also be used for assessment purposes. The optical-acoustic sensors in the apparatus 100 may be configured to measure for instance the range of motion and/or the reaction time of a user. Additionally, the apparatus 100 may be configured to obtain biofeedback in order to provide an assessment about the physical and/or sensing ability of the user.

The apparatus 100 is arranged to be used as a controller for a computing device based on signals received from the sensors. In particular, the apparatus is arranged to be used as a controller for a computer game, which may be configured to assist with training of hand and/or arm motor function. For example, the game may require a user to perform a certain hand and/or arm movement (such as flexion of the wrist) in order to move a character, and then perform a further functional movement (such as a grasping motion of the fingers) in order to perform an action in the game. In this case, data related to the functional movement is captured by the sensors and transmitted to the computing device, and the computing device is arranged to recognise that the data corresponds to the required functional movement (or otherwise).

Figure 9A:
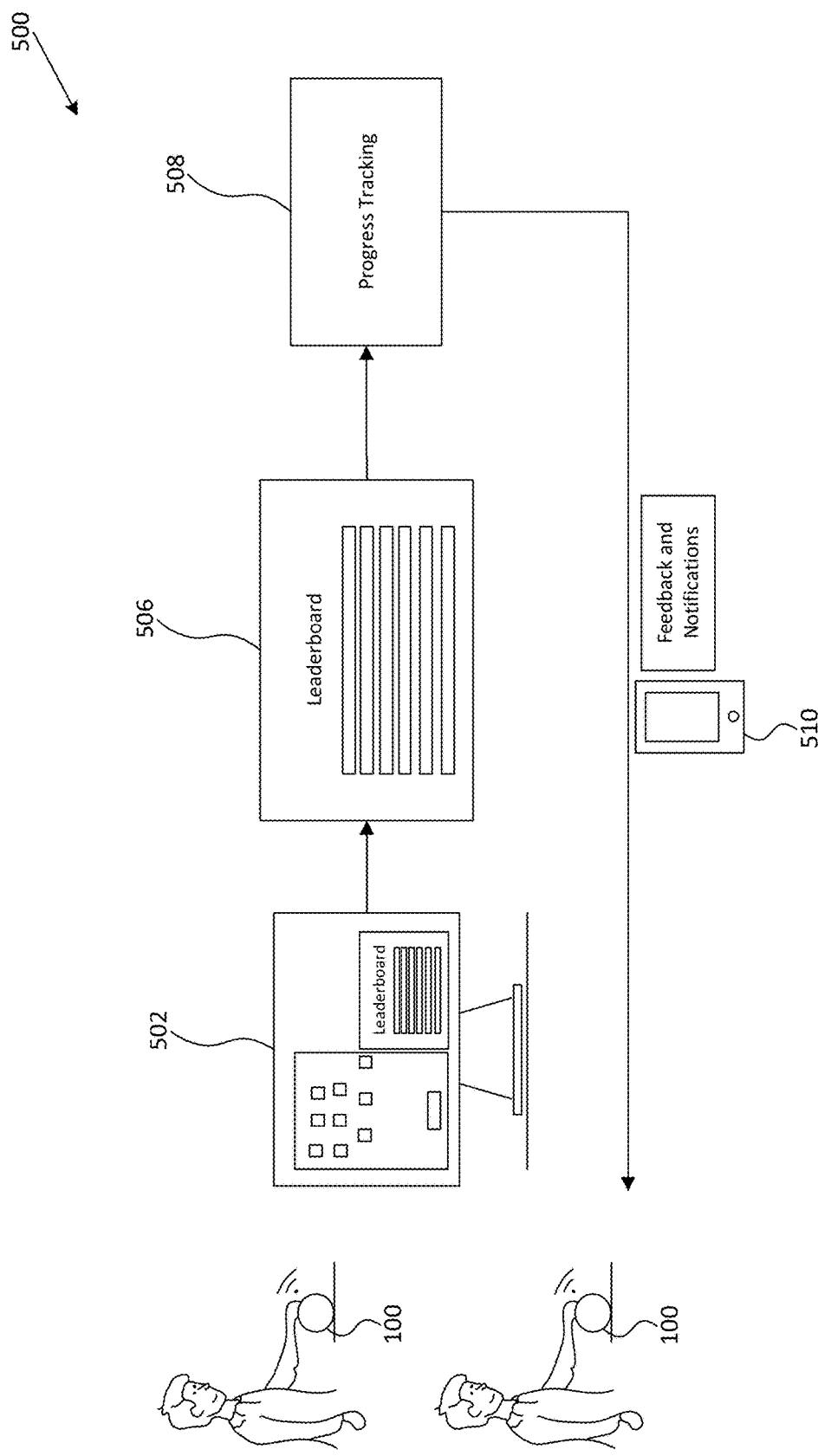
FIGS. 9A and 9B show a system incorporating several apparatuses.

FIG. 9A shows a system 500 for game playing incorporating multiple apparatuses 100. Multiple apparatuses 100 are able to act as a controller for a single computing device 502 implementing a multiplayer computing game. The use of a collaborative or competitive multiplayer game may improve a user's motivation to train using the apparatus. A leader board 506 (or other system showing results) may be used to show progress or results in the game. The results of the game and/or the raw data from the apparatus may be fed into a progress tracking module 508, which is arranged to calculate metrics related to the user's progress and training quality and/or quality, and provide feedback to the user, for example via a software application on a smartphone 510. It will be appreciated that the progress tracking module 508 and software app can also be used without the game to directly track and provide feedback about the user's training to the user, their carer and/or healthcare professionals.

Figure 9B:
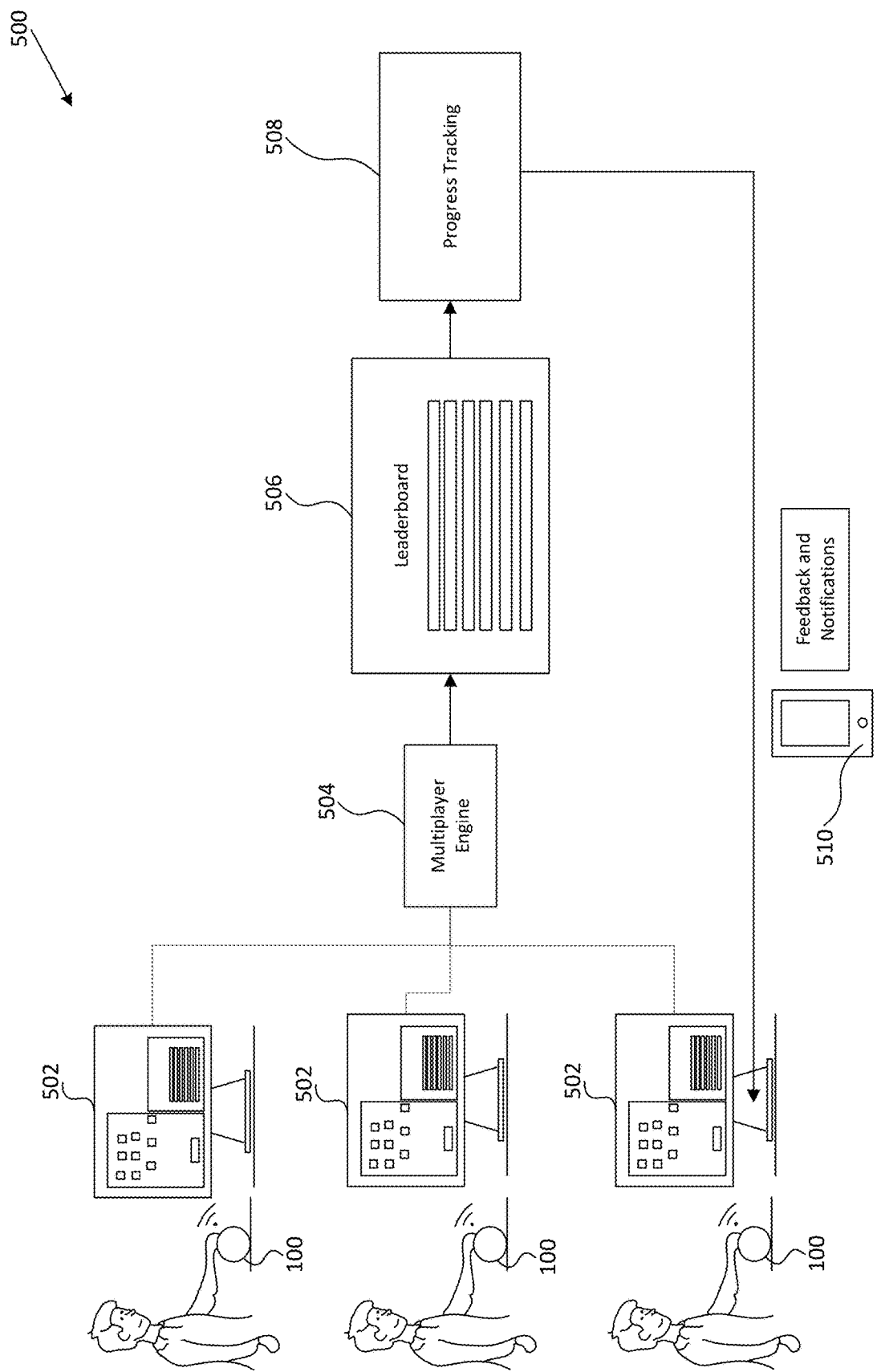

FIG. 9B shows another system for game playing incorporating multiple apparatuses 100. In an alternative, users who are not in the same physical location may each use an apparatus 100 as a controller for respective computing devices 502. A multiplayer engine 504 (which may be implemented online) may then be used to implement a multiplayer game, which is presented to each user using their computing device. Progress may be tracked as previously described.

Optionally, the user may play multiplayer games with another user using a different controller, such as a joystick or mouse and keyboard. This allows users having impaired motor functionality to interact with friends or family in an enjoyable way during their training.

The properties of the game (for example, difficulty) may be automatically adjusted to the needs of the user, for example based on an initial test arranged to determine the level of impaired motor functionality of the user. The test may also relate to any cognitive or sensing impairments that the user may have. The properties of the game may also be dynamically adjusted as the user is playing.

The computing device may be arranged to control the apparatus 100. For example, the computing device may be operable to selectively configure the number of degrees of freedom of the body 100 relative to the mounting 200. Alternatively, or additionally, the computing device may be configured to receive an input relating to relative movement of the body and the mounting where the input relates only to movement in one requested degree of freedom (which may be referred to as 'software filtering').

Optionally, the computing device is programmed with a video game.

Optionally, the computing device is programmed with a game designed especially for rehabilitation.

Optionally, the computing device is programmed with a modified existing video game, adapted especially for rehabilitation.

Optionally, the serious video game is a multiplayer game and the computing device is arranged to communicate with another computing device associated with another such apparatus.

Optionally, the serious video game is a multiplayer game and the computing device is arranged to communicate with many apparatuses simultaneously.

Figure 10A:
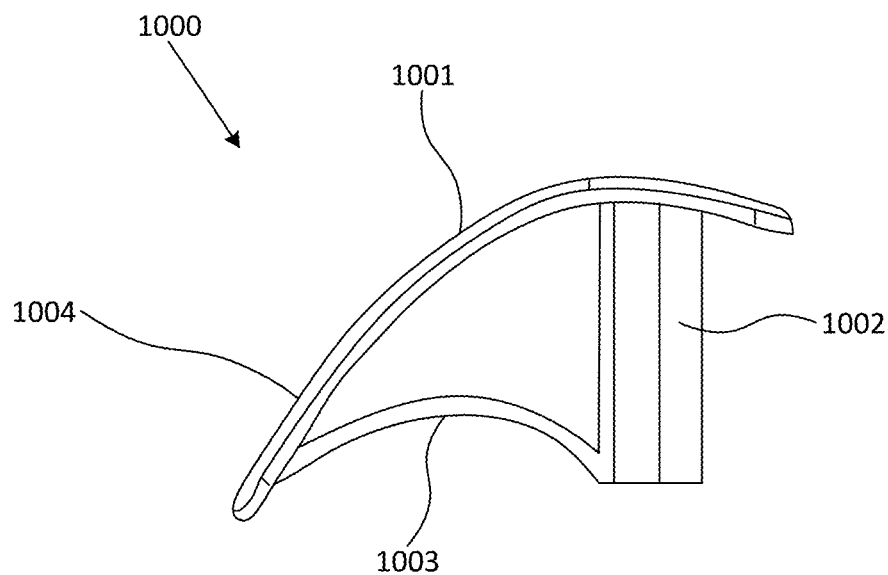
FIGS. 10A and 10B show an alternative finger support.
Figure 10B:
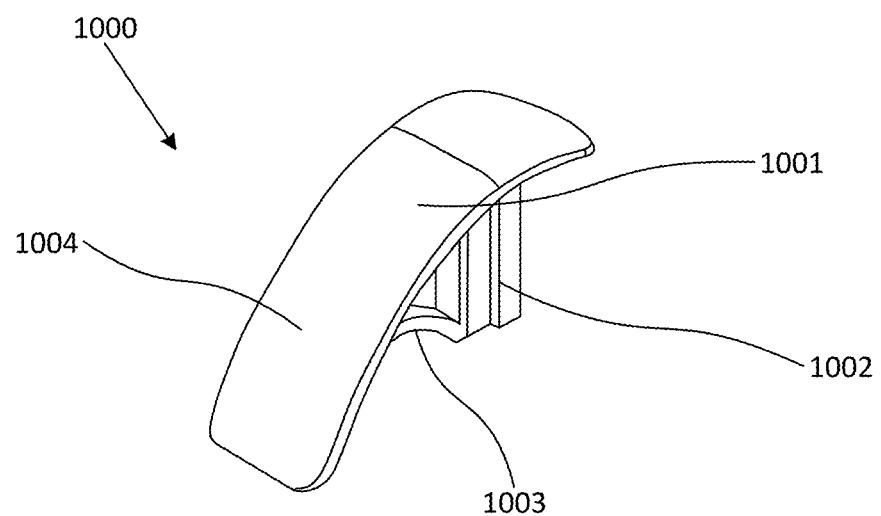
Figure 10C:
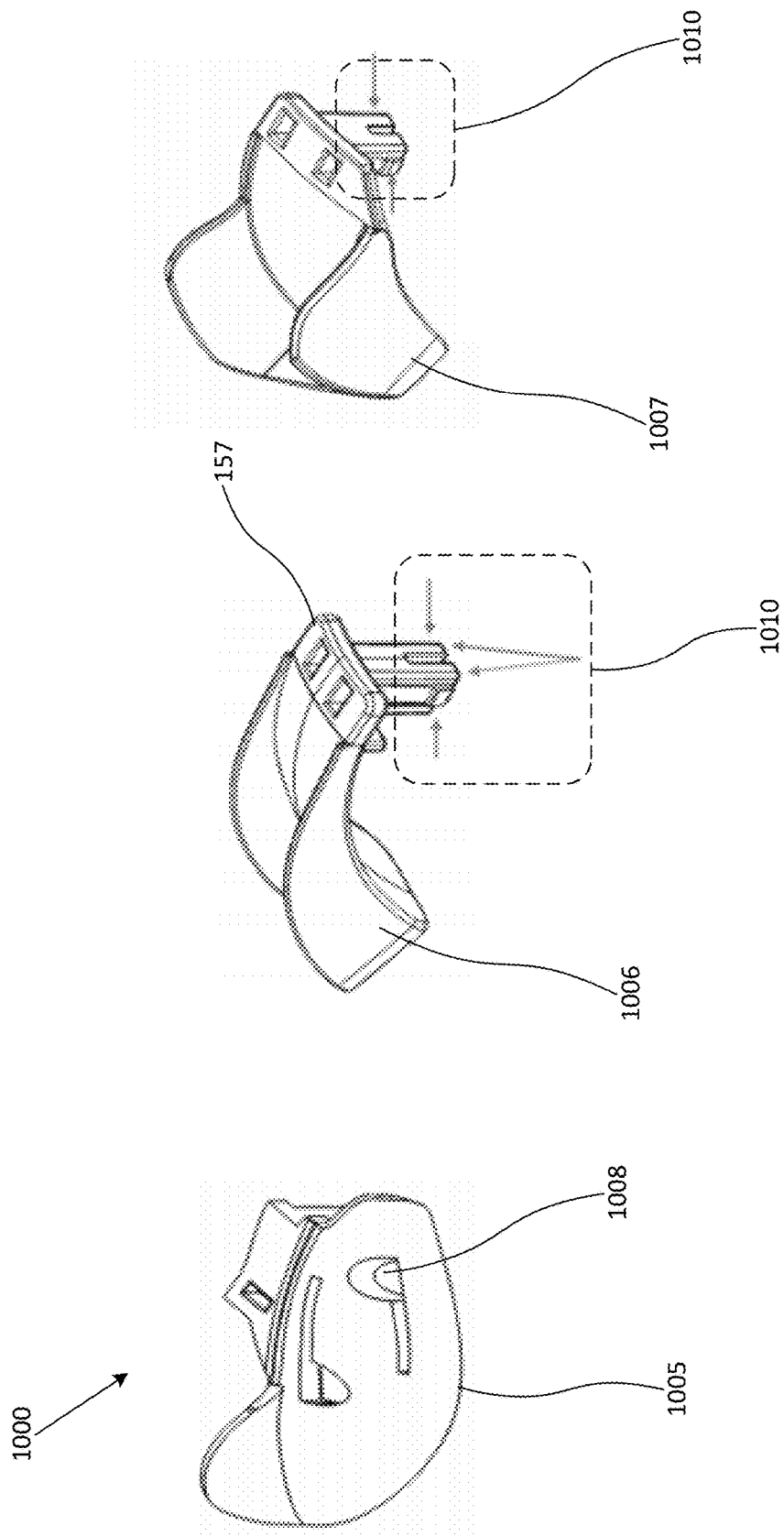
FIG. 10C shows a supplementary view of the finger support of FIGS. 10a and 10b.

FIGS. 10A to 10C show an alternative finger support 1000. The alternative finger support 1000 of this particular embodiment may comprise up to three portions, for example: a support portion 1001, an attachment portion 1002, and a resistance portion 1003. The alternative finger support 1000 may have any one or more of its three portions made of flexible material, which may include elastic or resilient materials, plastic, or metal. The support portion 1001 may take an elongated cuboid shape which is curved along the elongated face 1004. As shown in FIGS. 10a and 10b, the support portion 1001 is a curved surface which may support the finger of a user. It may be connected directly to the upper surface of the attachment portion 1002 and to one extremity of the resistance portion 1003. The attachment portion 1002 may be used to attach the finger support 1000 in the apparatus 100, and the attachment portion 1002 may slide into the apparatus 100. The pressure applied to the user's fingers may be resisted by the resistance portion 1003 and by the support portion 1001 itself.

FIG. 10C shows the alternative finger support 1000, comprising a support for a thumb and/or little finger 1005 (also referred to as a "pinkie"), a support for a middle finger 1006, and a support for a ring and/or index finger 1007. One or more of the supports 1005, 1006, 1007 may comprise an attachment mechanism 1010. The attachment mechanism 1010 can be used to attach or detach one or more of the supports 1005, 1006, 1007 from the base 110. If the attachment mechanism 1010 is correctly manipulated by squeezing and pushing the relevant parts of said mechanism, then the supports 1005, 1006, 1007 may be attached or detached, for example if replacement were necessary. The thumb or little finger supports 1005 may comprise openings 1008 to allow the attachment of straps, that can allow a user's thumb or little finger to be kept extended or in a comfortable position.

The resistance portion 1003 may take a generally curved shape and may be formed of flexible material. The side profile of the resistance portion 1003 may be generally arc-shaped. This resistance portion 1003 may be joined between a lower section of the attachment portion 1002 and the end of the support portion 1001. This may provide a resistance akin to a spring against a user's fingers, when the user flexes their fingers and the finger support bends, helping to keep the fingers open. This may be particularly useful when a user's hand suffers from spasticity. As can be seen particularly in FIG. 10a, the three portions (the support portion 1001, the attachment portion 1002, and the resistance portion 1003) when joined together, describe a hollow which may take the shape of a shark's dorsal fin.

In this alternative finger support 1000, the resistance may be provided by the combination of the resistance portion 1003 and the flexion of the support portion 1001, particularly close to attachment portion 1002. The pressure may be applied by the portion of the user's finger that is in contact with the support portion 1001. The peak of the pressure is expected to be in the point that the distal phalange (fingertip) of the user's finger is in contact with the support portion 1001. This is aided by the resistive portion 1003 to provide pressure against the user's fingertip (distal phalanx). By changing the thickness of at least one of the portions 1001, 1002 or 1003, then the resistance of the alternative finger support 1000 may change.

Figure 11A:
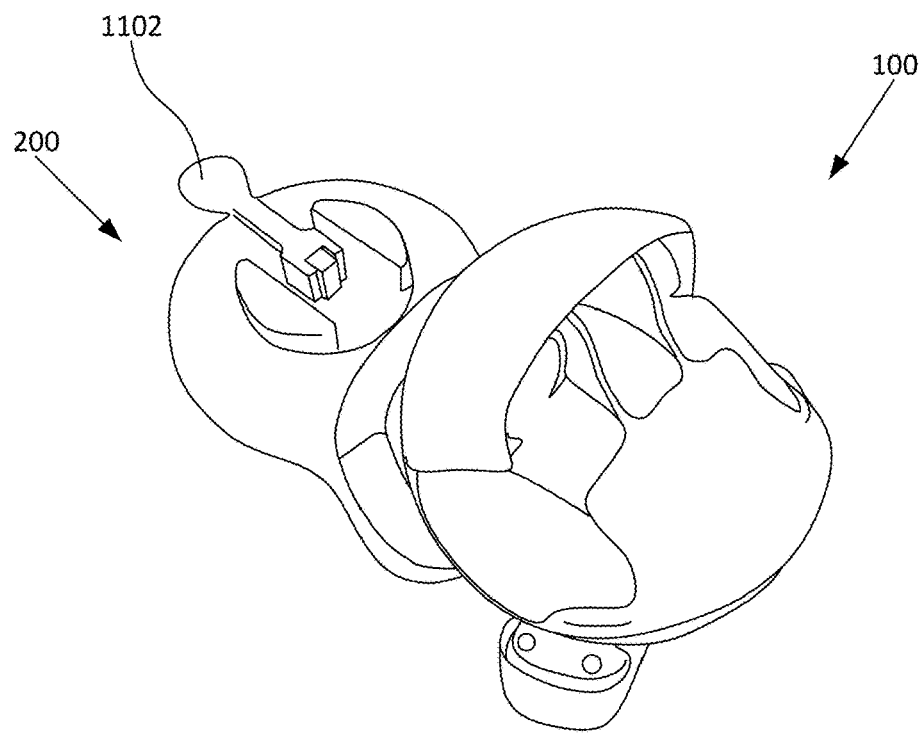
Figure 11B:
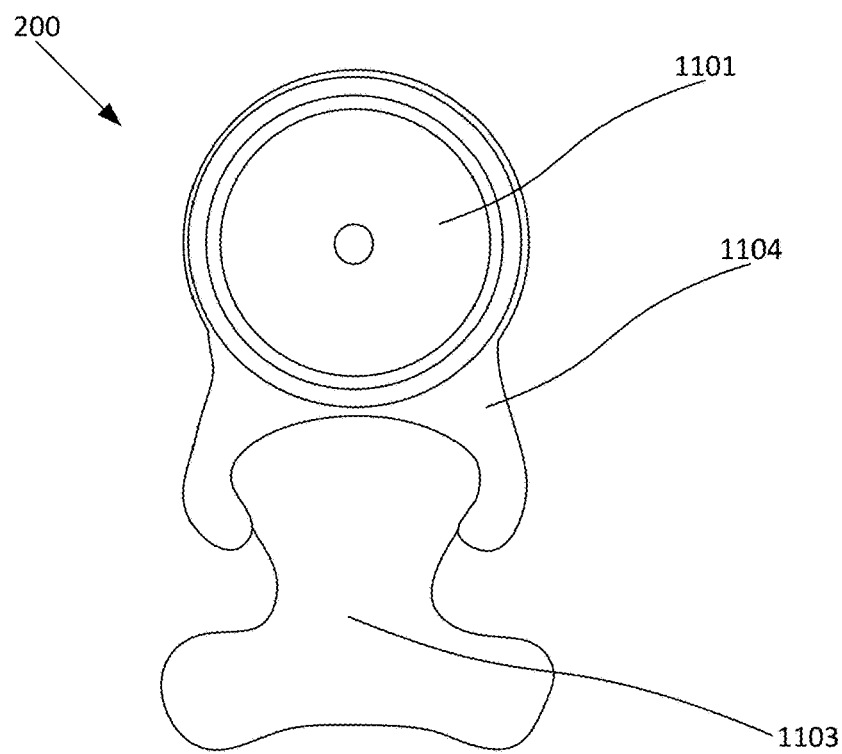

FIGS. 11A and 11B show an alternative mounting 200 for the apparatus 100. The alternative mounting 200 consists of a training arrangement 1103 and a fixing arrangement 1104. The training arrangement 1103 allows rotational movements of the wrist and the forearm, as mentioned before, while the fixing arrangement 1104 provides stability by fixing the apparatus 100 on the working surface. This mounting may be stabilised on a working surface (e.g. table) with the use of suction or vacuum cups, which may prevent the device from sliding and lifting. The user may place the apparatus 100 on a working surface, with the suction or vacuum cup 1101 making contact with the working surface.

In order to attach the apparatus 100 to the working surface, the vacuum cup 1101 may be moved between a first position in which the relative suction against the working surface is low and a second position in which the relative suction against the working surface is high. This movement may be by way of a handle 1102 which, when the vacuum cup 1101 is in the first position, may be vertical to the working surface. To move the vacuum cup 1101 into the second position, the user may press down the handle 1102, which may remove the air from the suction cup 1101, causing the mounting 200 to become affixed to the working surface. The reverse may also be applied, that is to say in the first position, vertical to the working surface, the handle 1102 may cause the mounting 200 to become affixed to the working surface, and in the second position, that is to say pressed down, the handle 1102 may cause the mounting to be released from the working surface.

Figure 11C:
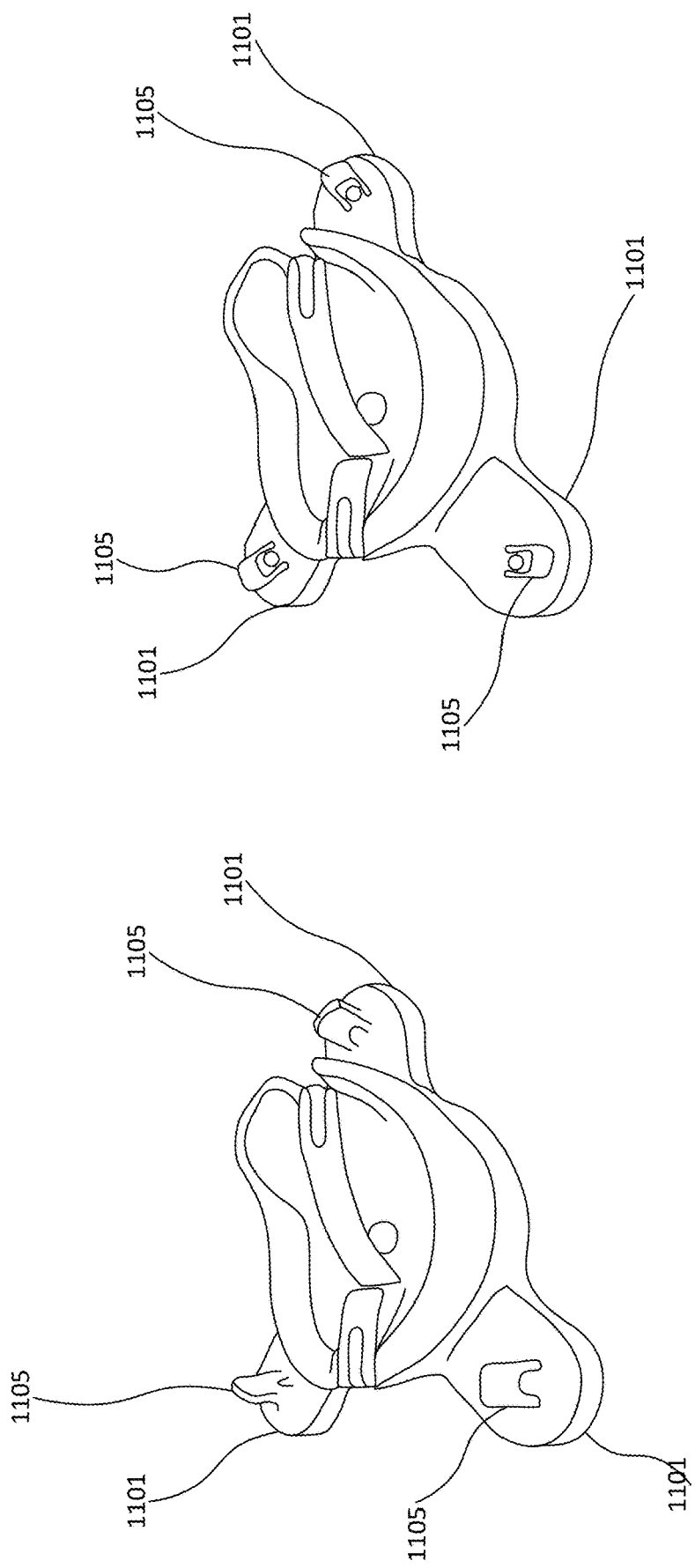
Figure 11D:
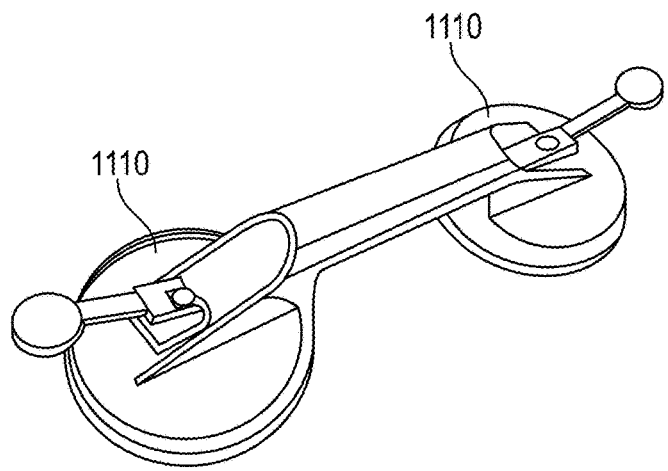

Alternatively or additionally the use of one or more bars 1105 can be employed to fix each of one or more vacuum cups 1101 separately onto a surface, as shown in FIG. 11C. FIG. 11C illustrates the use of one or more vacuum cups 1101 placed on the mounting which provide the level of minimal movement between the mounting 200 and the working surface. These may be easy to use but may not work for all surfaces. When the one or more vacuum cups 1101 are in the correct position, the bar 1105 can be orientated so as to lock the vacuum cup 1101 associated therewith into place.

Figure 11E:
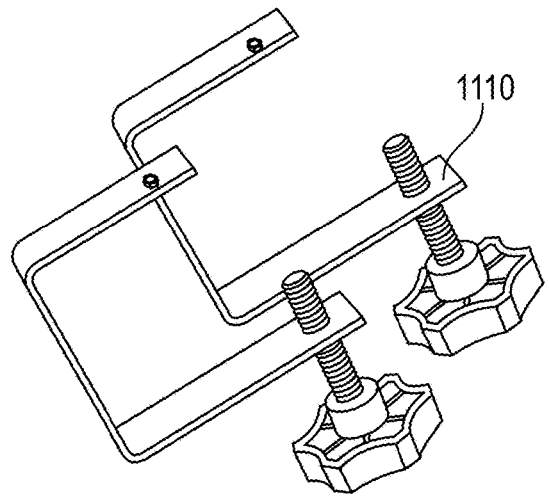

Alternatively, a clamp mechanism 1110 as shown in FIG. 11E may be used instead of a suction or vacuum cup 1101. Clamps 1110 may be used to fix the mounting 200 to a working surface as shown in FIG. 11E. These may provide a very stable mechanism but again may not work on some surfaces. For example, users may not wish to clamp wooden tables because of damage that may occur.

Additionally, as shown in FIG. 11B, the training arrangement 1103 may be detachable from the fixing arrangement 1104, to allow a user to make a choice as to whether extra stability is required. In that way the training arrangement 1103 can slide on a working surface, for example a table, and allow the user to train both elbow and shoulder flexion and extension in a reaching movement.

Furthermore, during a training session the apparatus 100 may be required to be fixed or at least be immoveable or substantially immoveable relative to the working surface (e.g. a table). For example, while a user puts their hand on the apparatus, it is convenient if the mounting remains stable. Additionally, the user may need to focus only on wrist training without moving the arm, and so again the mounting may be required to be stabilised. The mounting may be stabilised using one or more of the methods disclosed herein. The base 110 may still be operable to freely move on the mounting 200, so that a user can train their wrist. A locking mechanism may be used such that the base does not move with respect to the mounting, and thus users with hand and/or arm problems such as tremors or weak hands can put their hands on the device without excess assistance.

Figure 11F:
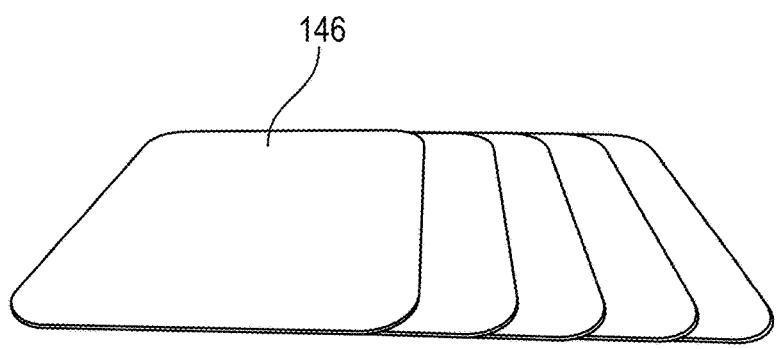

Alternatively, friction pads 146 (also referred to as "friction mats") such as Dycem® may be used, being integrated to the bottom part of the mounting. The integration may comprise the friction matts being glued or self-adhered to a bottom part of the mounting. In one embodiment, six such friction pads are used. Even if one pad fails, the movement of the mounting may still be reduced to an acceptable level during use. Alternatively, any other suitable material which creates friction may be used to minimise the movement of the apparatus relative to the working surface. This is illustrated in FIG. 11F. Friction mats are relatively easy to use but may prove not sufficiently stable, especially when applying forces parallel to the working surface.

Figure 11G:
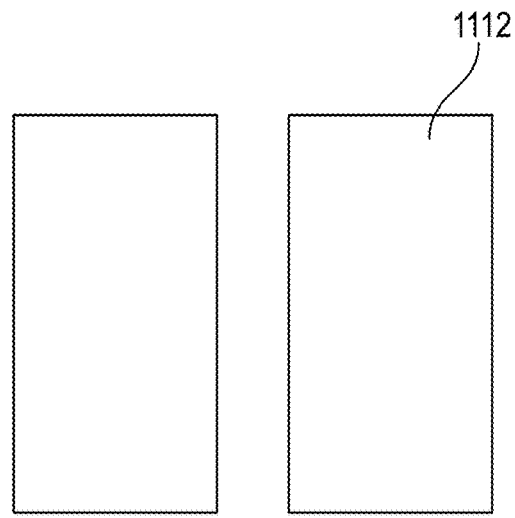
Figure 11H:
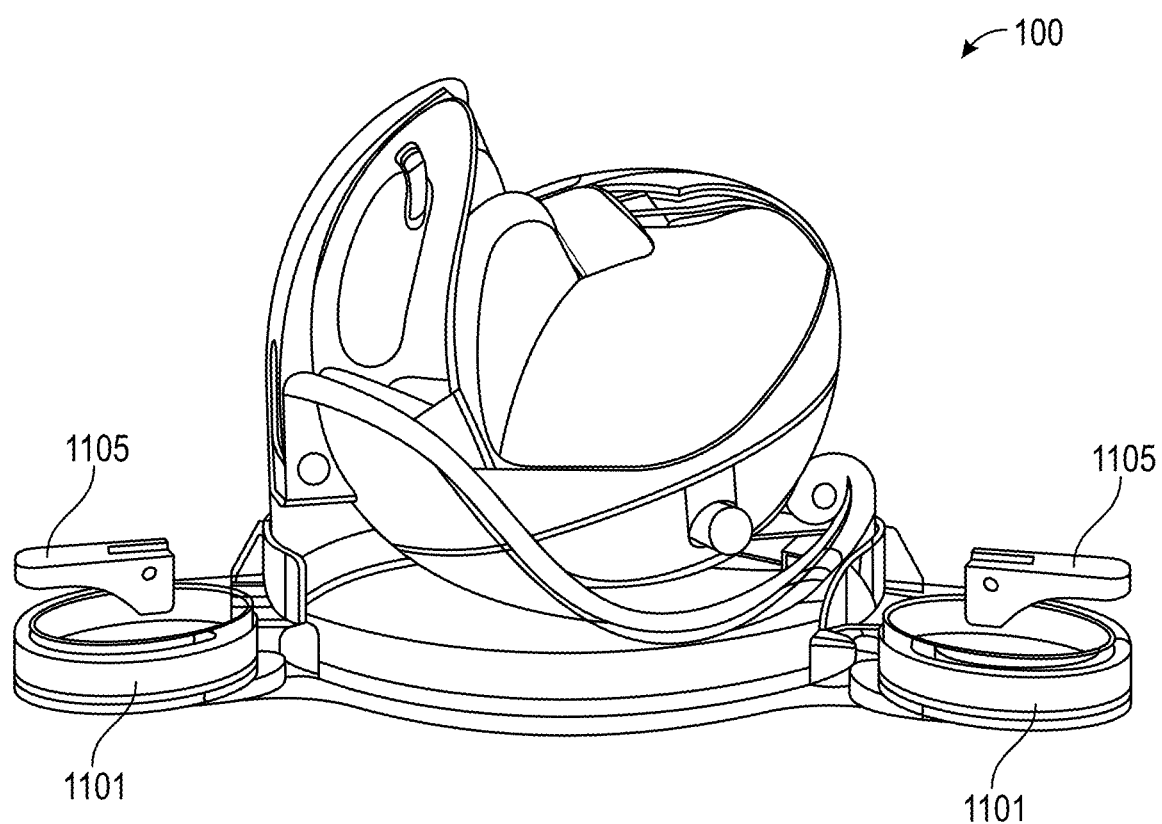

As a further option, as shown in FIG. 11G, Velcro® pads 1112 may be used. These are relatively easy to use and very stable. However, they are a permanent feature and may damage the working surface.

It may be understood by the skilled person that a combination of the various mounting systems may be used as desired. For example, as shown in FIGS. 11H to 11K, a mounting system comprising three suction cups and/or one or more non-friction mat pads to provide the desired level of stability and fix the device to the working surface. The one or more friction pads 146 may be adhered to the surface of the mounting 200 adjacent the working surface upon which the apparatus 100 is to be used.

Figure 12:
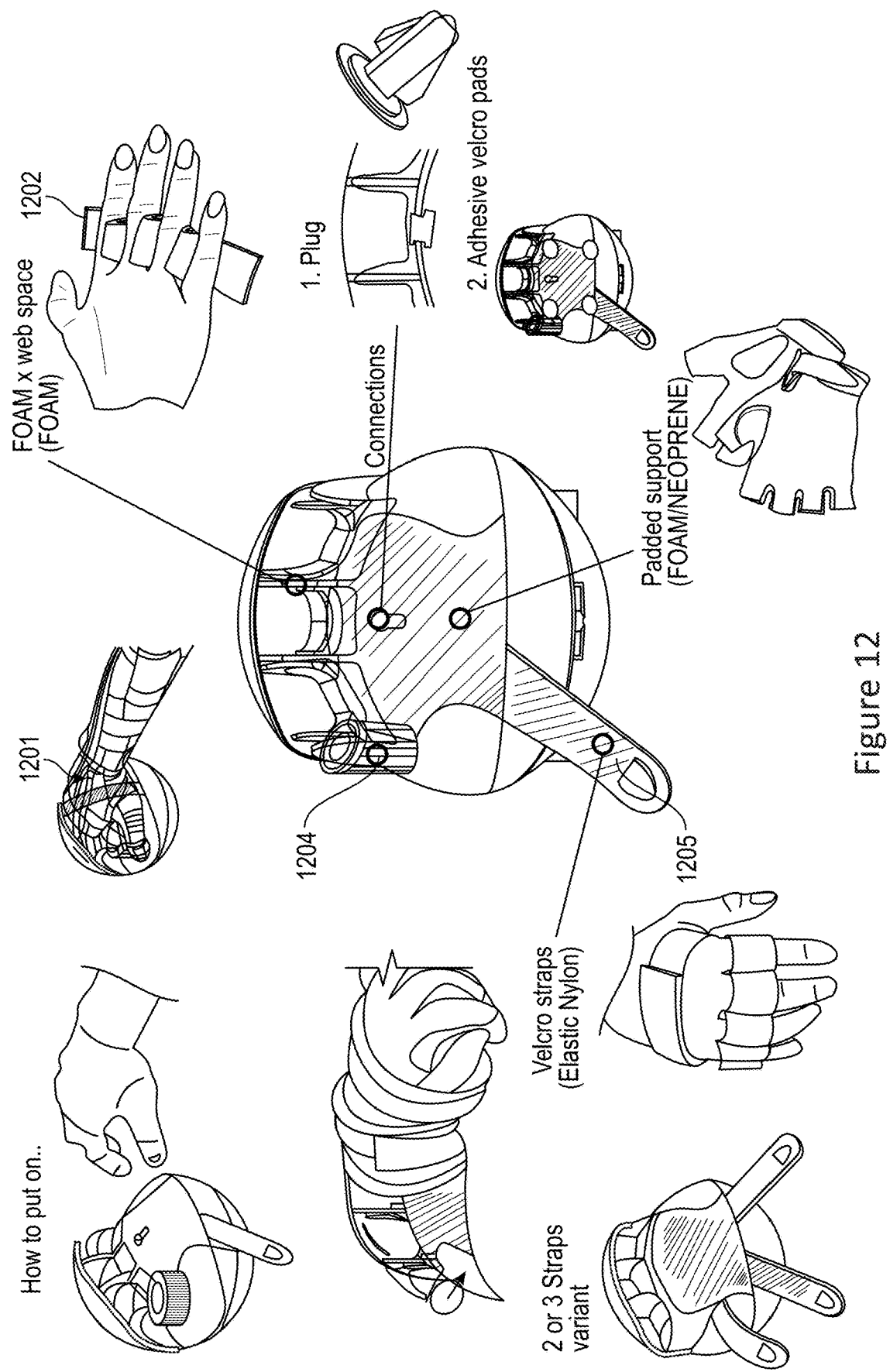
FIG. 12 shows a strap attachment for the apparatus.

As shown in FIG. 12, a strap 1205 may be mounted appropriately on the base 110 to increase comfort and/or stabilise the hand on the base. The strap 1205 may be made of any comfortable fabric or material. This may serve to increase the comfort of the device on the user's palms, knuckles and/or the web spaces of the fingers and/or help the user put the hand on the device. By fixing a strap on a hand controller, the controller may be made more comfortable to use, easier to clean as the strap may be removed and cleaned in a conventional manner, easier to be use by different patients in clinics and hospitals as the straps may be considered consumables and hence disposed of when required, and less expensive to be manufactured. Producing an overmold through injection moulding, or coating the controller with a soft material, may in some circumstances be much more expensive to produce than a material strap.

Some strap 1205 configurations may be arranged to keep the hand of a user in an optimum position according to a medical professional, by preventing the movement of the hand sliding right or left on the apparatus. A wrist strap, which may for example comprise a snap band, may be included as part of a strap arrangement, as some users (for example stroke survivors) may choose to put the wrist strap on first, so that their fingers are close to the slots and their hand stays on the device. They may then find it more convenient to put each finger separately in the finger slots. In some embodiments, one or more straps may be used to facilitate users putting their hand on the device, as well as making the using of the device itself more comfortable and keeping the hand steady on the device once it has been placed thereon.

The strap also has the added benefit that it can secure the user's hand on the base, thus minimising the risk of dropping the base for example during bimanual training. Furthermore, the strap may improve the quality of the training session. In some embodiments, separate straps may be available to accommodate a user's thumb and fingers, and secure them to the base. In such embodiments, the thumb or finger straps may be connected to an appropriate finger support, and/or mounted adjacent a thumb support recess.

Figure 13A:
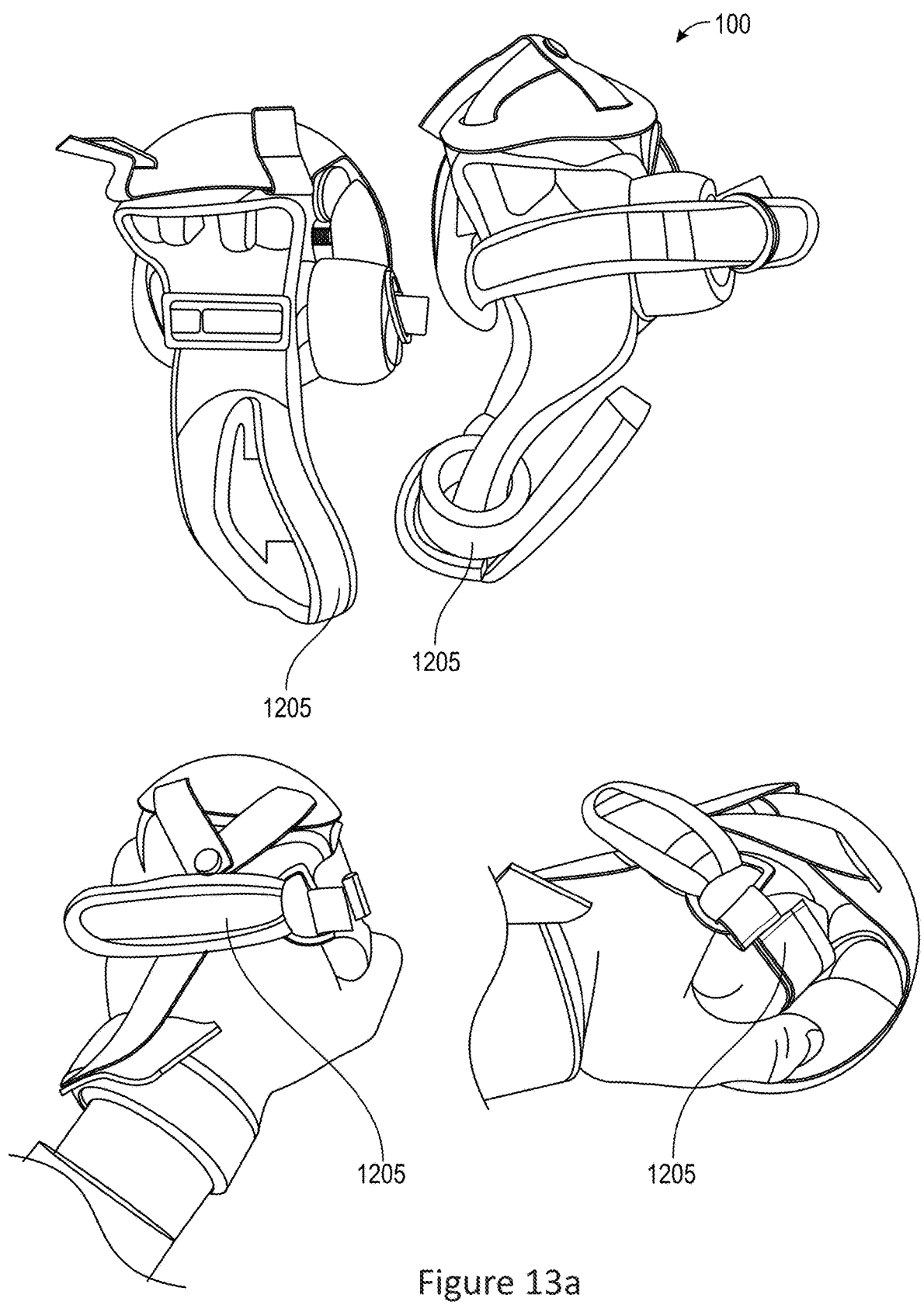
FIGS. 13A and 13B show a range of strap arrangements.

FIG. 13A illustrates a variety of different types of straps.

Figure 13B:
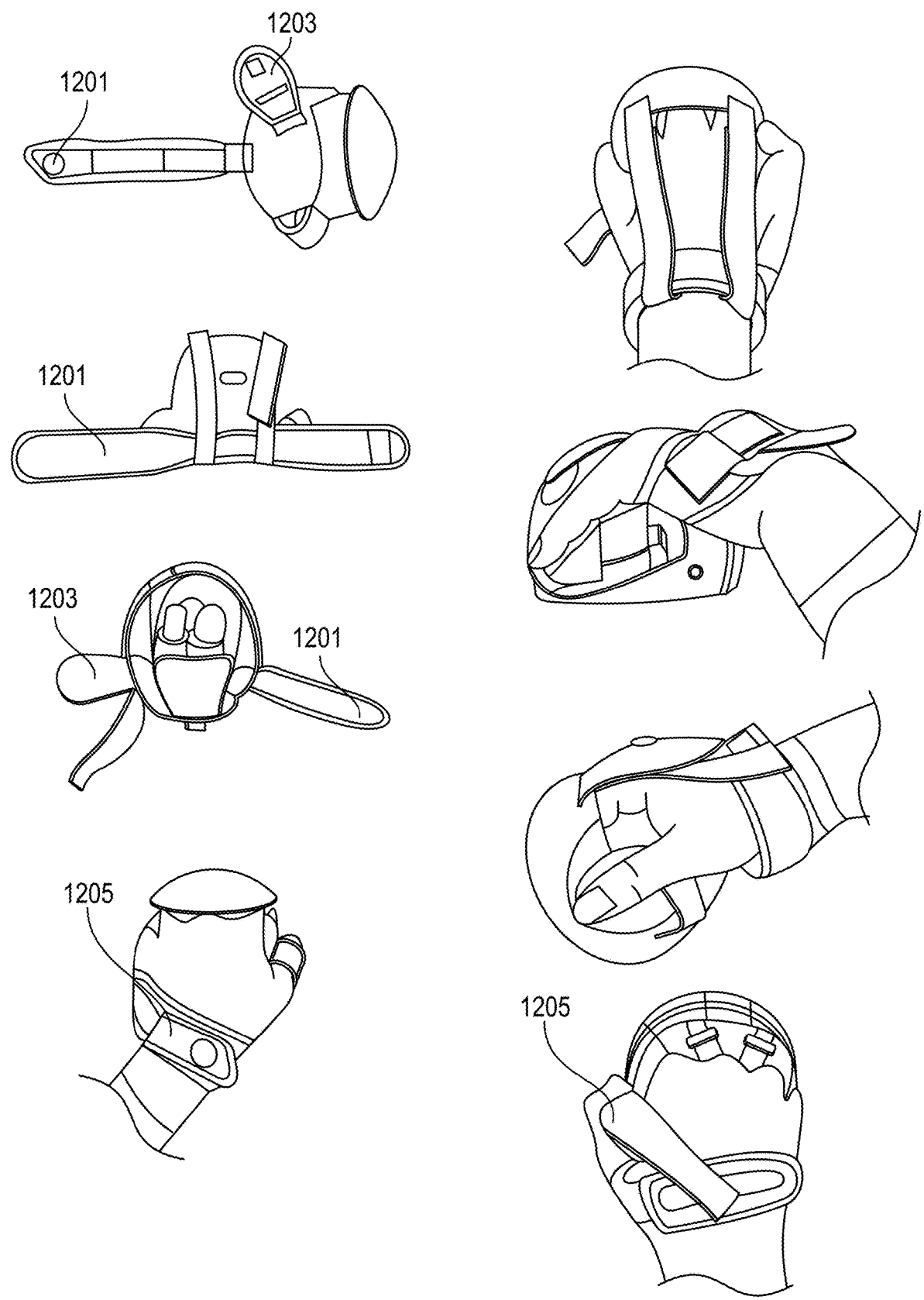

FIG. 13B shows a further embodiment of the strap 1205. The strap comprises from a longer wrist strap 1201 which is used to secure the wrist of the user and a shorter strap 1203. The wrist strap 1201 may join the 1203 through a clasp and/or hook and loop fastener arrangement to form a single main strap 1205. Both straps may be made of a pliable material. Additionally, both straps 1201 and 1203 may have Velcro on them, so that the user is able to hold them easily together, before fixing them, for example by passing the wrist strap 1201 through the loop of the wrist strap 1203.

Any straps used 1205 may be detachable from the base 110. This may facilitate the cleaning of the device. The strap 1205 may be made of a washable fabric or material making it suitable for washing in a washing machine. The strap 1205 may be coupled to the base using one or more buttons, or other fixing means. The base 110 may also comprise openings that allow the straps to slide in easily.

The strap 1205 may be provided with a thumb spacer 1204. The thumb spacer 1204 may serve to keep the thumb of the user in an extended position. Alternatively, a second strap, either attached to the base or to the main strap (or to both) can be used, in order to keep the thumb extended or separate it from the other fingers. This feature may be of assistance to disabled users that suffer from hand spasticity. The thumbs of such users tend towards always being flexed and this feature may provide a comfortable way of extending the thumb.

The strap 1205 may allow disabled users, for example stroke survivors, to secure their wrist more easily by using their non-paretic hand. This function may be achieved through the use of snap bands or bracelets or semi-rigid materials inside the strap portion that is placed around the wrist. The snap bands or bracelets or semi-rigid materials may be inside a strap, but may also be independent and attached to one or more straps. Users can thereby place the strap around their wrist easily, by using one hand only.

The strap 1205 may also allow the user to secure their wrist before putting the fingers into the device. The strap may serve to help ensure that the hand of the user does not slip from the base and also keeps their fingers close to the openings. For this purpose, a strap may be provided that surrounds the wrist and is connected to the base, and hence is arranged to push the fingers inside their respective slots.

The strap itself may apply forces in two separate directions:
1. Towards the finger slots: In one embodiment, the user can pull the strap and connect it to a wrist strap, thereby pushing their fingers inside the base 110, optionally comprising a substantially spherical hand controller. This helps the hand to be placed within and then stay inside the device.
2. In a further embodiment, there is provided a strap operable to push down the hand of a user on the base. The hand is therefore urged against the base.

The use of the strap provides the benefits of allowing a user with an impaired hand to wear a glove-like device.

Figure 13C:
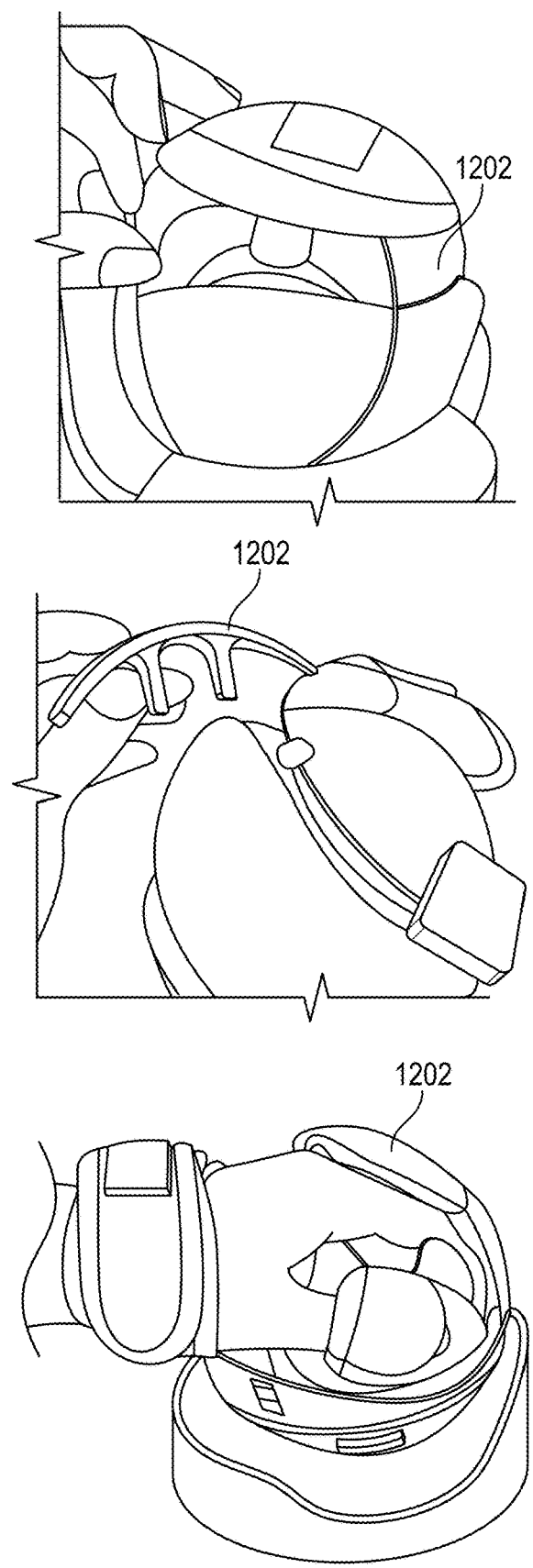
FIG. 13C shows a support optionally for use to improve comfort for a user.

As shown in FIG. 13C, the base may further comprise a silicone-based support 1202, optionally coupled to the strap, to alleviate discomfort during use. It is appreciated that the support may be formed alternatively or additionally from thermoplastic polyurethane (TPU), thermoplastic elastomer (TPE), foam, and other materials with suitable properties. The silicone-based support 1202 may be a separate, replaceable, component from the base and may in particular cushion the knuckles of a user's hand.

Figure 14A:
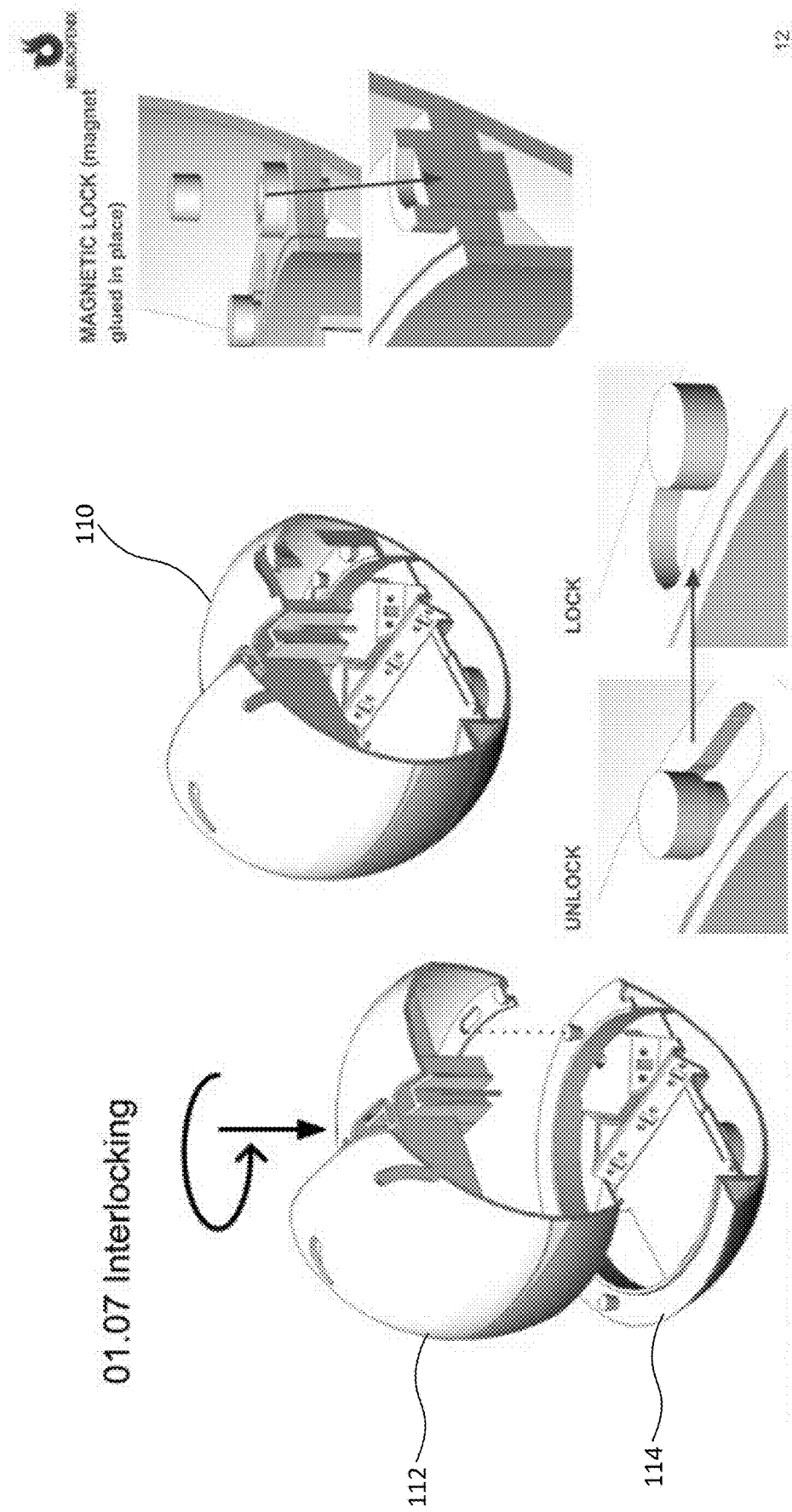
FIG. 14A shows an embodiment of the device whereby the top and bottom hemispheres of the base are easily separated.
Figure 14B:
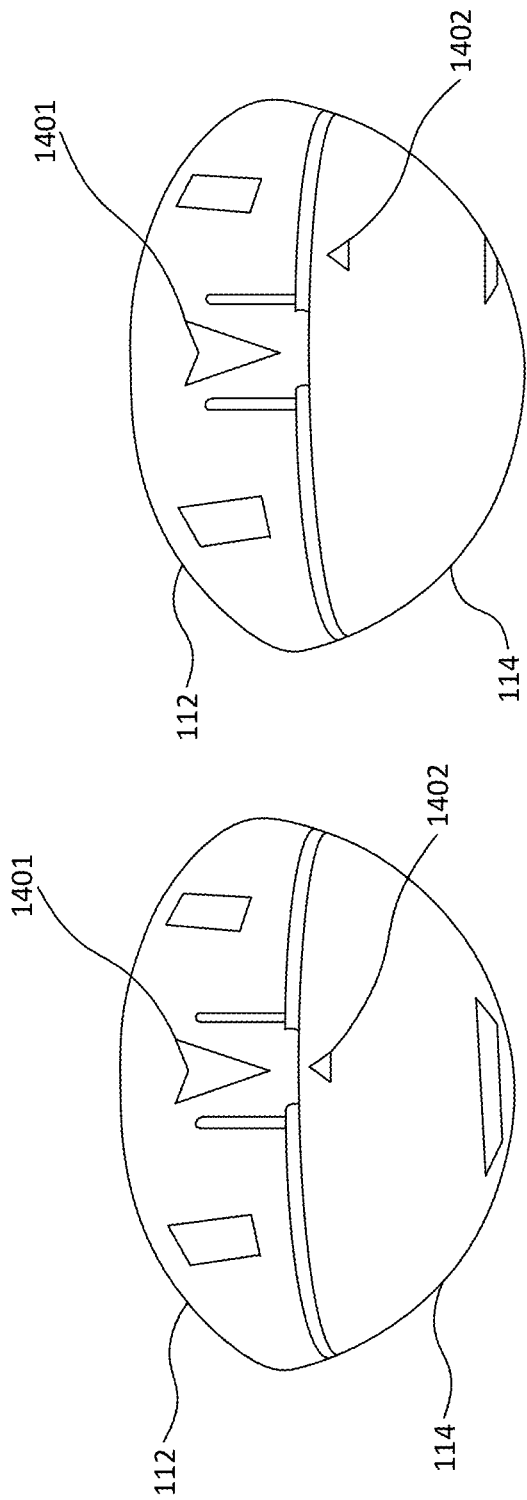
FIG. 14B shows an external view of the embodiment of FIG. 14A.

FIG. 14A illustrates an embodiment of the device whereby the upper 112 and lower 114 hemispheres of the base are easily separated. The electronics may be situated in the lower hemisphere, thus allowing the top hemisphere to be removed without impacting the function of the device. In such an embodiment, the base comprises two main parts, the top and bottom hemisphere. The electronics of the base and/or any other electronic components used in relation to the base may all be contained within the bottom hemisphere. The electronics of one embodiment comprise: the main printed circuit board (PCB), five smaller PCBs comprising LIDAR range finding chips, a battery, and one or more LEDs. The LEDs may be arranged in a strip, or be provided in a single unit of one LED. It will be appreciated that multiple LED arrangements are possible. FIG. 14B shows an embodiment further comprising two arrows 1401, 1402, which are fixed to the upper 112 and lower 114 hemispheres respectively. When the arrows 1401, 1402, are aligned then the hemispheres are connected. A user can then press on the arrow 1401 fixed to the upper hemisphere 112, and then rotate the upper hemisphere 112 to unlock the two hemispheres. The arrows 1401, 1402, are then no longer aligned. The hemispheres may be unlocked to facilitate cleaning. It is understood that any logo, icon, symbol, or phrase, may be used in place of the arrows 1401, 1402 to perform a similar function.

This hemisphere's main functions may comprise the following:

1) The orientation of the bottom hemisphere (and hence the device as a whole) can be inferred through the sensor fusion of linear and rotational acceleration over time. Linear acceleration is measured by an accelerometer and rotational accelerometer is measured by a gyroscope. Both the accelerometer and the gyroscope are contained within a single chip called an Inertial Measurement Unit (IMU) on the PCB within the bottom hemisphere. The orientation of the bottom hemisphere is transmitted to the central microcontroller (MCU) for processing and optional transmission to aa computing device.

2) The positions of the user's fingers are inferred through the use of five LIDAR range finding chips. These are mounted on small PCBs separate to the main PCB. These small PCBs each have five conductive pins on the back which stick out beyond the border of their PCBs. The "flying" ends of these pins slot through and are soldered to the main PCB, providing electronic connections. The angles of these small PCBs are set by resting them against a support before soldering, ensuring they point in the correct direction for measuring the user's finger distance when the user has their fingers within the top hemisphere and the hemispheres are connected together. The range finding chips then measure the time-of-flight of an infrared laser between the face of the chip and the underside of the support under a user's finger. As the user closes their fingers to make a fist, the distance between the underside of their finger support and the chip decreases. Opening the user's hand will increase this distance. Distance data is sent from the LIDAR chips to the MCU for processing and optionally transmission to a computing device.

3) One or more LEDs around the bottom hemisphere circumference provides visual cues and feedback to the user. This is controlled by the MCU. The one or more LEDs may be surrounded by a translucent material which allows at least a portion of the light generated to pass through.

4) A central microcontroller (MCU) acts to collect all peripheral sensor data, process it and transmit it to a Bluetooth module for transmission to the software platform. The MCU additionally controls the indicator LEDs around the bottom hemisphere circumference, measures battery voltage, controls the Bluetooth module and optionally parses incoming data requests from an associated software application. The combination of the orientation and finger position tracking allows the bottom hemisphere to act independently as a data collection unit, sensing acceleration, orientation and 5-directional distance through the LIDAR chips. The top hemisphere may be electronically inert and, in such cases, would act only to stabilise the user's hand in the frame of vision of the LIDAR chips, while facilitating the extension of the user's fingers and/or the training of finger flexion and/or extension. In other embodiments the top hemisphere comprises one or more additional sensor functions.

It is therefore understood that potential uses of this bottom hemisphere extend beyond the scope of use described in relation to the rehabilitation of the hand of a user, and may include: any treatment wherein the bottom hemisphere is placed on a balance board to detect orientation and train the balance of a user; being strapped around a user's chest, waist, legs, arm, head and/or neck to increase exercising options; attaching different parts where the top hemisphere would normally attach, providing alternative functionalities for the LIDAR sensors; and/or used as a virtual reality or augmented reality controller or input device.

As can be seen in FIGS. 14A and 14B, the device is provided with an interlocking joint that enables the separation of the two halves of the device. As a result of this feature the top hemisphere that contacts the user's hand is completely interchangeable and can be easily cleaned as a separate part. This feature enables the device to be adapted for a variety of hand sizes (and/or levels of impairment for patients), by changing only the top hemisphere and retaining the bottom hemisphere. This feature may also enable a therapist/clinician to use just the bottom hemisphere for all patients with a separate upper hemisphere for each patient.

Furthermore, this feature enables the replacement of the top hemisphere (which is the one that is most used) whenever it has worn out.

In an embodiment wherein the bottom hemisphere comprises the electronics core, the top hemisphere may be considered disposable and as such can be personalised to each user according to their level of impairment, hand size, and/or other individual consideration and ergonomics. Thus, the bottom hemisphere may additionally be used in other applications, for example:

Placing the bottom hemisphere on a balance board to play one or more games in an accompanying software package to train the user's balance;

Adding straps to the bottom hemisphere and strapping it around the user's chest, waist, legs, arm, head and/or neck to increase the available exercising options;

Attaching differently shaped or equipped parts as top hemispheres that use the at least one of the bottom hemisphere sensors for different functionalities; or Using the described optical wireless finger sensing technology in relation to a virtual reality (VR) or augmented reality (AR) experience.

In an alternative arrangement a magnetic lock may be provided. In this embodiment a magnet is glued in place on the lower hemisphere and the upper hemisphere may be provided with a metallic strip which when it contacts the magnet may serve to lock the upper and lower hemispheres together.

Figure 15:
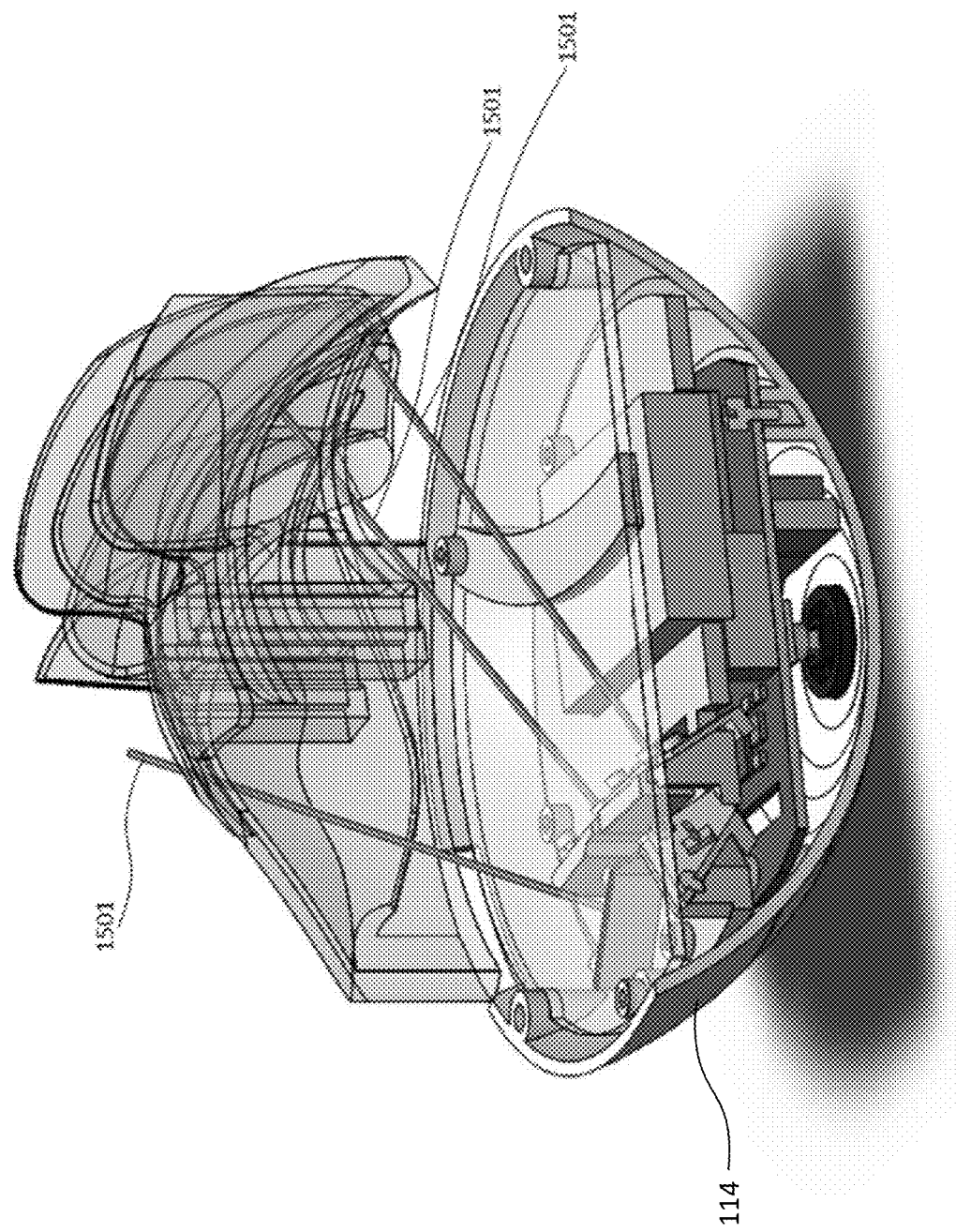
FIG. 15 shows a sensing system for tracking finger displacement.

FIG. 15 illustrates a sensing system that tracks the finger displacement. The sensor may be wired or wireless. Examples of suitable sensors are lidar, reflective or optical sensors located in the lower hemisphere to detect any displacement of the finger supports. In the case of the sensor being an optical sensor, a laser beam may be used. In FIG. 15 laser beams 1501 impinge on the finger supports and are used for sensing the displacement of the finger supports. In FIG. 15 only three beams are shown, however it will be understood that one for each finger support may be utilised.

Of course, it will be understood that other types of sensors can also be used. An individual sensor for each finger support may be used or a configuration that allows the device to sense a user's grip may also be implemented.

Hall effect sensors may be used to detect the relevant position of at least two different points in each finger support. This may provide very accurate detection of the displacement of the finger supports.

Figure 16A:
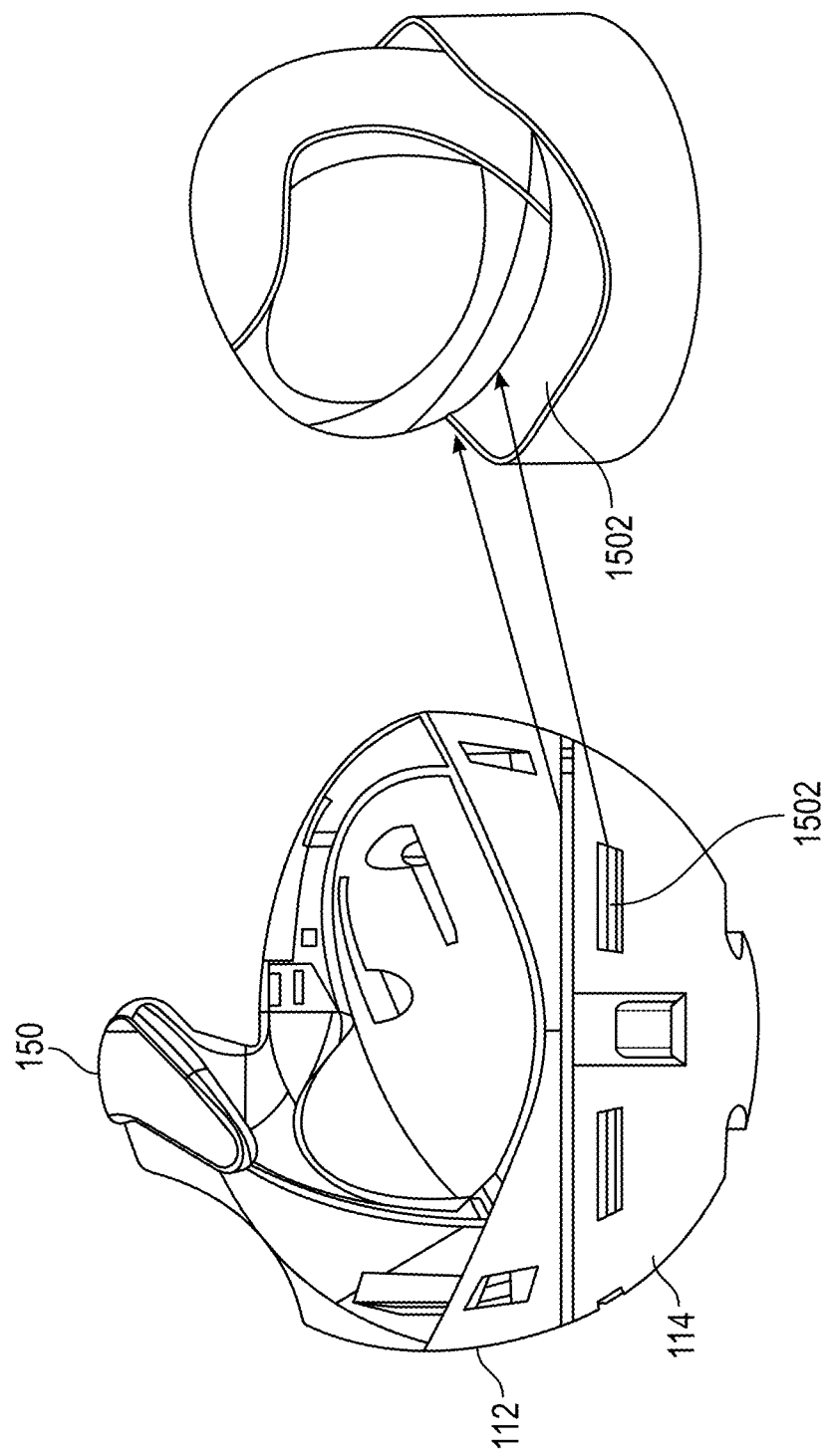
FIGS. 16A and 16B show the use of an LED or other light for visual feedback.
Figure 16B:
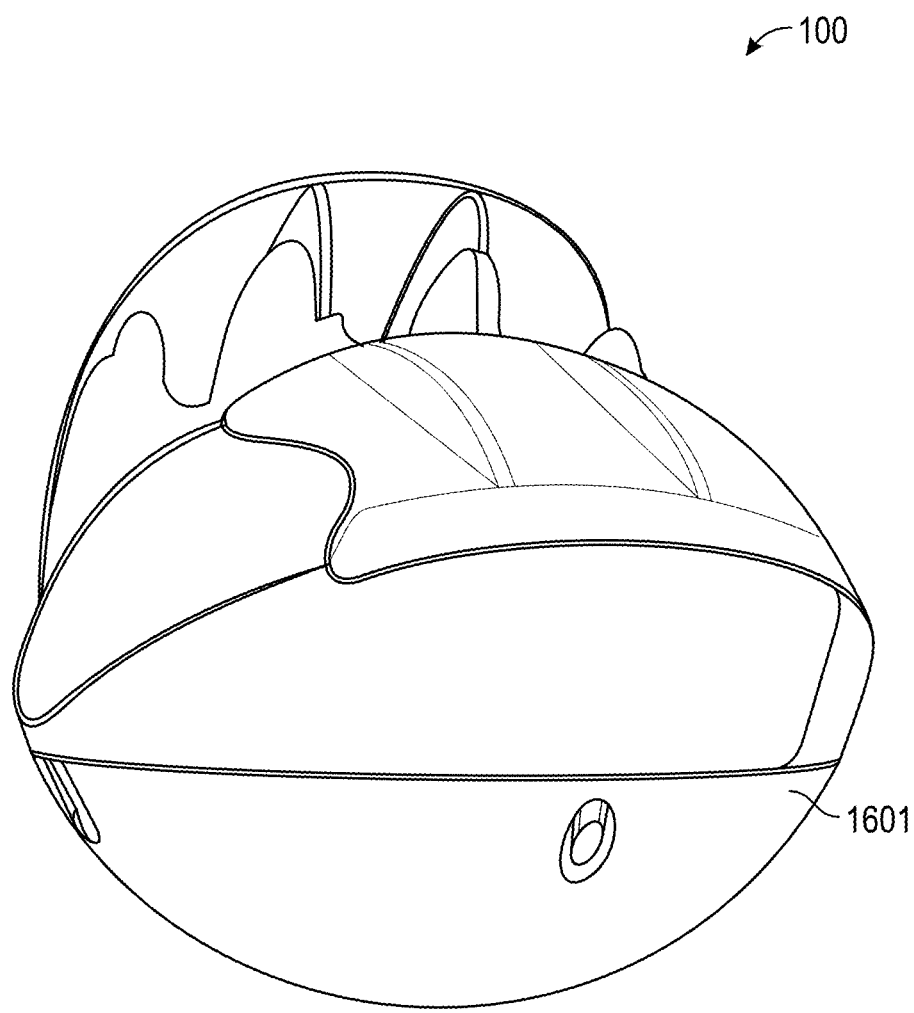

FIGS. 16A and 16B illustrate the use of an LED or other light for visual feedback. The LED 1601 may be placed on the base or on the mounting to provide feedback to the user, whereby an indication of whether the device is turned on/off may be given. LEDs may also be used to provide visual feedback of other indications, such as for example, technical problem/s with the device (Bluetooth connection is lost) or as feedback related to a game or a training movement. The bottom hemisphere 114 may comprise transparent parts 1502 to provide more visual feedback.

Figure 17:
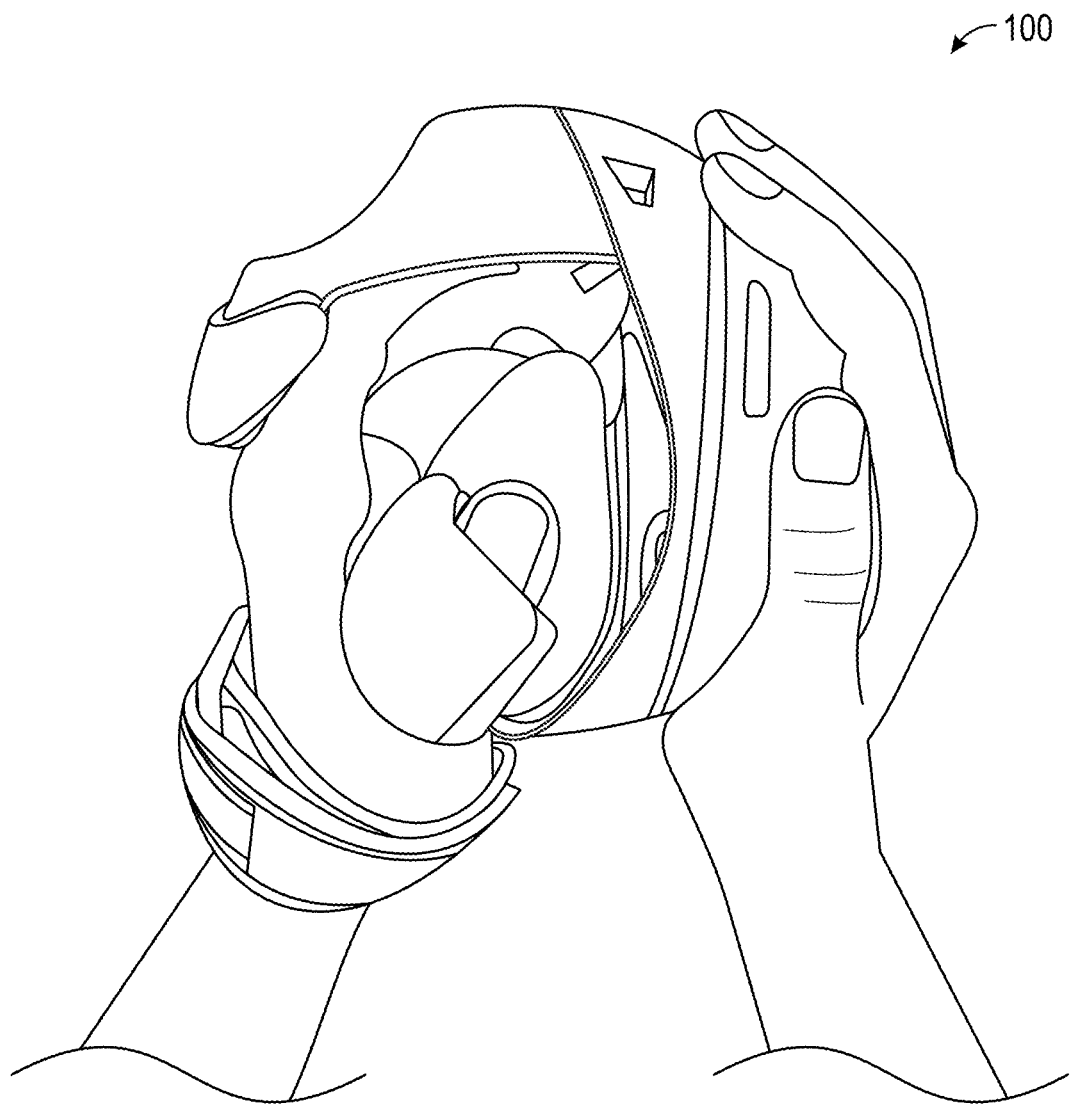
FIG. 17 shows an embodiment of the apparatus operable to be used by two hands of a user simultaneously.

FIG. 17 illustrates the use of the apparatus 100 as part of a bimanual training exercise. It is understood that one or more of the embodiments outlined herein may be used to train two hands of a user, or two separate users, simultaneously.

Further, the apparatus 100 may be used as a computer mouse, 5-finger keyboard, joystick and/or other Human Interface Device (HID). More specifically, patients or healthy people may employ the device to interact with a digital platform owing to the stability, comfort, and ease of use.

It is to be understood, however, that such application may also not be limited to stroke survivors. The apparatus 100 may be used as a peripheral device, for instance to play computer or interactive games, as an input device for VR or AR platforms, to control robotic industrial devices, to control a drone or drones, and/or as a finger training device to improve skills in activities such as climbing or guitar playing.

It will be understood that the device may be used with other technologies in order to maximise the rehabilitation potential. Particularly where the user is a stroke patient, the device may be combined with Functional Electrical Stimulation whereby a current stimulates the hand of the user to enable the user to move their fingers in a direction. Electromyography (EMG) sensors may be placed on a user's hands to detect their intention to move their hand which may be used as an input for the training movements. Alternatively, the sensors may be used as an input for playing games.

The device may be equipped with microphones for audio feedback. This may assist users who have impaired sight. This mechanism may make the use of a computing device optional.

Alternatives and Extensions

It will be appreciated that although the various aspects have been principally described with reference to users having suffered strokes, it will be appreciated that the described aspects can be used with any user seeking to train hand and/or arm movement, particularly for rehabilitation after a loss of motor function—for example as a result of an injury which may include a spinal cord injury, or for example as a result of cerebral palsy, multiple sclerosis, other neurological conditions, osteoarthritis, rehabilitation after hand surgery or microsurgery, physical rehabilitation after reconstructive surgery (where e.g. a finger's nerves have been reconnected and need to re-grow properly), muscular dystrophies, paralysis due to herniated vertebral disc, among other physical and neurological impairments that results in loose of control and/or weakness and/or stiffness of the upper (and lower) limb.

In an alternative or in addition to the use of compliant finger supports 150, the finger supports may be urged into a neutral position. For example, the finger supports may be solid (i.e. formed from a non-compliant material) and may pivot about a connection point to the body 110 or at one or more joints in the finger support. Each of the finger supports may then be attached to a spring, which returns the finger support to a neutral position when the finger support is displaced by a user. A string or wire may extend between the spring and finger support, where the springs are internal to the body. The stiffness and/or starting position of the springs may be adjustable to suit the needs of each particular user, for example by use of one or more rotatable knobs attached to the spring.

Optionally, the finger supports are arranged to be deployed by a user from a stored position into the neutral position, for example by a user pressing a button. The finger supports may be deployed from a stored position then is, in use, under the user's fingers, so that the action of the finger supports being deployed into the neutral position assist in opening the user's hand. For example, the finger supports may be attached to the body in the same position (optionally, via the recesses 118) as described, but at an angle with respect to the neutral position. Providing deployable finger supports may allow a user suffering from spasticity to place their hand on the apparatus more easily, and may also assist in hand release. Optionally, finger supports may be attachable to the body in the stored position while the user's hand is already on the body 110.

Optionally, the thumb recess 118*e* may have the same size and shape as the other recesses 118, such that the thumb support is interchangeable with the finger supports 150.

Optionally, the body 110 includes a yet further recess 118*d* and a yet further thumb recess 118*e*, which are respectively arranged on the opposite side of the body to the further recess 118*d* and the thumb recess 118*e*. This may allow the apparatus 100 to be set up for use for a user's left hand or right hand interchangeably.

Optionally, the finger support 150 comprises a mixture of compliant and non-compliant materials. For example, only the joints 162 of the member 152 may be formed from a compliant material, while the remainder of the finger support is formed from a non-compliant material. The size and stiffness of the joints may be adjusted by replacing the compliant material portions used as the joints.

Optionally, the characteristics of the finger support, in particular the stiffness of the member, are adjustable while the finger support is in situ on the body. For example, each finger support may comprise an adjustable tensioner which allows the stiffness of the member to be adjusted.

Optionally, the angle of the finger support (and thereby the neutral position) is adjustable, for example by allowing the angle of the entire portion of the upper hemisphere 112 having the recesses 118 to be adjusted by the use of a rotatable knob.

The support loop 164 may alternatively be formed as a slip having a pair of resilient jaws, which may be biased towards each other. This may allow a user's finger to be received through the jaws from above (when pressed on one or both of the jaws, or a flange extending outwardly from the jaws, to overcome the bias of the jaws), thereby improving a user's ability to place their hand and fingers easily on the device.

Optionally, the upper hemisphere 112 and lower hemisphere 114 of the body 110 are arranged to be rotatable relative to each other, thereby to allow a user to train a functional gripping and twisting motion (similar to a motion of gripping and twisting a door knob), in particular when the apparatus is used in an unsupported mode (i.e. where the user supports a hemisphere of the body using each of their hands). The hemispheres may be sprung relative to each other, such that the relative twisting of the hemispheres is resisted. Such relative hemispherical rotation may also be used in allowing for the device to be pivoted about the z-axis (i.e. abduction and adduction of the wrist).

Optionally, different materials may be used for the finger supports 150, and by way of an example, there may be a first material which provides stiffness X, a second material which provides stiffness 2X and a third material which provides stiffness 3X.

Although the various aspects have generally been described with reference to training hand movement, they can be used for other parts of the body—in particular, the described aspects may be applied to training foot and/or leg movement, in particular ankle mobility, which exhibits a similar number of degrees of freedom as the wrist.

In an alternative, finger supports 150 may not be used with the body 110. Instead, grooves for supporting a user's fingers may be provided, optionally with a button at an end of the groove for measuring grip strength. A similar embodiment is depicted in FIG. 8.

Optionally, the finger supports 150 may not move with respect to the body 110, such that the apparatus 100 may serve to open and separate the fingers of a user. The apparatus 100 may be placed on a table and moved in a similar fashion to a mouse for a computer or other similar input device. Alternatively, the apparatus 100 may be held in the hand or hands of a user (that is to say bimanually), in order to train only the wrist. In such a scenario, a mounting 200 may not be required.

Alternatively, means other than the described springs may be used for assisting and/or resisting the rotation of the body 110 relative to the mounting 200. For example, one or more motors may be provided to drive the rotation of the ball in a particular direction.

Optionally, haptic sensors are used in the body 110 in order to provide feedback to the user, based on sensor data. Hot and/or cold sensors may be added to the device to provide haptic feedback. Examples of such sensors are Peltier sensors which can change the temperature of the finger supports, providing haptic feedback to the user.

The body 110 may further comprise an internal battery for powering the sensors and control circuitry, which is contained in the cavity 130. Optionally, the battery is arranged to be charged wirelessly, for example via the mounting 200 (which may be connected to a mains electricity supply)

Optionally, the movement of the body 110 in 3D space is tracked using a camera, for example a camera of a smartphone or tablet. Such movement data may be incorporated into the previously described games system.

Optionally, the movement of the body 110 in 3D space may be tracked using at least two arm bands, each of which includes at least one gyroscope. One band may be placed on the forearm and one may be placed on the shoulder. These bands may optionally also include an accelerometer and/or magnetometer. Such movement data may be incorporated into the previously described games system.

Optionally, the apparatus further comprises an arm support for at least partially supporting the upper limb the user is aiming to train.

Optionally, this device may be used for rehabilitation after finger, wrist, elbow or shoulder physical injury, for people with no neurological impairment.

Optionally, this device may be used for strength training or training that aims to increase the range of motion of the user's limb.

It will be understood that the invention has been described above purely by way of example, and modifications of detail can be made within the scope of the invention.

Additionally, it will be understood that in the present description, the axes referred to are in the Cartesian coordinate (x, y, z) system.

Each feature disclosed in the description, and (where appropriate) the claims and drawings may be provided independently or in any appropriate combination.

In one embodiment, the apparatus as disclosed herein is provided alongside a central software platform comprising games for rehabilitation and/or training. The software may provide goal-setting features, rewards and social features such as a community. This centralized software platform may be equipped to connect with different electronic devices including the apparatus disclosed herein and any associated trackers or sensors. The software may further be operable to:

Connect with many sets of apparatus, or just the bottom hemispheres that contain the electronics as in one embodiment;

Connect with different training devices that each train one or a set of movements from one or multiple joints of the body.

Connect with different training devices to train one or a set of body functions (swallowing, speech, walking, jumping, etc.) which are likely to be impaired after a stroke or a neurological injury.

Target patients with different levels of impairment, for example using different sets of apparatus for users with mild upper limb impairment compared to users with severe upper limb impairment;

Classify one or more users based on the inputs from a plurality of different hardware devices;

Allow the users to share scores, audio-visual material, progress and/or medical information; provide a gamification framework to increase attachment to therapy, for example goal-setting, habit forming, rewards systems, and/or video games; and allow users to compete and collaborate through games by creating a community.

Reference numerals appearing in the claims are by way of illustration only and shall have no limiting effect on the scope of the claims.

The invention claimed is:

1. An apparatus for training hand movement, comprising:
a base arranged to support a hand of a user from a palm side of the hand;
at least one finger support provided on the base, each finger support comprising a support joint corresponding to a finger joint of a respective finger of the hand of the user, the support joint enabling bending of said each finger support over a range of motion that mimics a range of motion of the finger joint of the respective finger;
a finger and/or hand restraint having one or more discrete openings, the guide formed from a rigid or semi-rigid material, wherein each of the one or more discrete openings is positioned in alignment with each of the at least one finger support;
at least one sensor configured to measure, for the at least one finger support, an initial position of the support joint and a final position of the support joint during a training movement; and
a controller configured to determine one or more metrics corresponding to a range of motion of the finger joint for at least one finger of the user based on the initial position and the final position of the support joint for a corresponding finger support;
wherein the at least one finger support is independently movable at the support joint as a result of applying pressure to the at least one finger support by the respective finger of the hand.

2. The apparatus according to claim 1, wherein the support joint of the at least one finger support is arranged to allow the hand to exert a grasping motion on the base.

3. The apparatus according to claim 1, wherein the support joint of the at least one finger support is arranged to allow an extension movement to be exerted thereon by the finger of the user.

4. The apparatus according to claim 1:
wherein the support joint of the at least one finger support has a neutral position relative to the base, said at least one finger support being arranged to resist movement away from the neutral position;
wherein the support joint of the at least one finger support is formed from a resilient material thereby configured to resist movement away from the neutral position.

5. The apparatus according to claim 1, wherein the at least one finger support comprises two or more finger supports configured to move independent of one another.

6. The apparatus according to claim 5, wherein the base comprises a plurality of mounts for the two or more finger supports, wherein the mounts are configurable to attach at least one of the two or more finger supports to the base such that the apparatus can selectively be used by both a left-handed and a right-handed user.

7. The apparatus according to claim 5:
wherein the at least one finger support includes an index finger support corresponding to an index finger of the user, a middle finger support corresponding to a middle finger of the user, and a ring finger support corresponding to a ring finger of the user;
wherein the controller is configured to determine the one or more metrics for the first finger joint in each of the index finger, middle finger, and ring finger of the user.

8. The apparatus according to claim 1, further comprising:
a thumb support configured to position a thumb of the user in a stationary position during the movement; and
a pinkie support configured to position a pinkie of the user in a stationary position during the movement.

9. The apparatus according to claim 1:
wherein the finger joint includes at least one of a proximal interphalangeal (PIP) joint and a human metacarpophalangeal (MCP) joint; and
wherein and one or more metrics include at least one of a range of motion of the human PIP joint and a range of motion of the human MCP joint.

10. The apparatus according to claim 1, wherein the at least one finger support is detachable from the base.

11. The apparatus according to claim 1, further comprising a mounting arranged to receive the base, whereby the base is movable relative to the mounting.

12. The apparatus according to claim 11, wherein the base and mounting are arranged such that movement of the base relative to the mounting is configured to be restricted to at least one of x, y and z axes of rotation, wherein the base is pivotable relative to the mounting about either: a single axis of rotation or two axes of rotation.

13. The apparatus according to claim 11, further comprising a modular block, wherein the modular block is operable to restrict movement of the base relative to movement of the mounting.

14. The apparatus according to claim 11, wherein the mounting may be positioned such that axes of rotation about which the base can move are respectively aligned with a direction of a motion of the hand of the user when in use.

15. The apparatus according to claim 11, wherein the motion of the base relative to the mounting is arranged to simulate at least one of the following movements: wrist flexion/extension; forearm pronation/supination; and wrist ulnar and radial deviation.

16. The apparatus according to claim 11, the mounting comprising an underside portion, the underside portion operable to be placed upon a support surface, and the mounting further comprising at least one friction pad wherein the at least one friction pad is provided on the underside portion of the mounting.

17. The apparatus according to claim 11, further comprising:
at least one base sensor for acquiring data related to movement of the base relative to the mounting;
wherein the controller is configured to determine one or more metrics corresponding to movement of at least one of the wrist and the forearm.

18. The apparatus according to claim 1, wherein the one or more metrics corresponding to a range of motion of the finger joint includes a grip strength metric.

19. A kit of parts for training hand movement, comprising:
a base for supporting a hand of a user from a palm side of the hand;
at least one finger support provided on the base, each finger support corresponding to a respective finger of the hand of the user, the support joint enabling bending of said each finger support over a range of motion that mimics a range of motion of the finger joint of the respective finger;
at least one sensor configured to measure, for the at least one finger support, an initial position of the support joint and a final position of the support joint during a training movement; and
a controller configured to determine one or more metrics corresponding to a range of motion of the finger joint for at least one finger of the user based on the initial position and the final position of the support joint for a corresponding finger support;
a first mounting arranged to receive the base; and
a second mounting arranged to receive the base, the first mounting and the second mounting being interchangeable;
wherein the first mounting is arranged to allow movement of the base relative to the first mounting about a different number of axes of rotation than the second mounting as a result of applying pressure by the hand.

* * * * *